(12) United States Patent
Babbs et al.

(10) Patent No.: US 10,806,679 B2
(45) Date of Patent: Oct. 20, 2020

(54) SYSTEMS AND METHODS FOR TUBING DELIVERY

(71) Applicant: AbbVie Inc., North Chicago, IL (US)

(72) Inventors: Kellan William Babbs, Grayslake, IL (US); Nolan Harrington Baird, III, Johnsburg, IL (US); Antonio Juan Belton, Richton Park, IL (US); Sean Joel Corrigan, Chicago, IL (US); Charles Michael Galitz, Kenosha, WI (US); Thomas Paul Grazier, Spring Grove, IL (US); Daniel Joseph Greene, Chicago, IL (US); Keith Aaron Grider, Chicago, IL (US); Thomas Joseph Huemann, Round Lake, IL (US); Wayne Phillip Klingler, Lindenhurst, IL (US); Michael Honsing Lau, Chicago, IL (US); Tomas Andrius Matusaitis, Chicago, IL (US)

(73) Assignee: AbbVie Inc., North Chicago, IL (US)

( * ) Notice: Subject to any disclaimer, the term of this patent is extended or adjusted under 35 U.S.C. 154(b) by 677 days.

(21) Appl. No.: 15/401,468

(22) PCT Filed: Jul. 10, 2015

(86) PCT No.: PCT/US2015/040001
§ 371 (c)(1),
(2) Date: Jan. 9, 2017

(87) PCT Pub. No.: WO2016/007890
PCT Pub. Date: Jan. 14, 2016

(65) Prior Publication Data
US 2017/0209344 A1    Jul. 27, 2017

(30) Foreign Application Priority Data

Jul. 10, 2014    (WO) ................ PCT/US2014/046229

(51) Int. Cl.
*A61J 15/00* (2006.01)
*A61M 39/10* (2006.01)
(Continued)

(52) U.S. Cl.
CPC ....... *A61J 15/0026* (2013.01); *A61J 15/0015* (2013.01); *A61J 15/0053* (2013.01);
(Continued)

(58) Field of Classification Search
CPC ................ A61J 15/0026; A61J 15/0015; A61J 15/0076; A61J 15/0053; A61J 15/0069;
(Continued)

(56) References Cited

U.S. PATENT DOCUMENTS 4,152,017 A    5/1979 Abramson
4,685,901 A    8/1987 Parks
(Continued)

FOREIGN PATENT DOCUMENTS

CN        101754743 A    6/2010
DE    10 2009 048 584 B3    4/2012
(Continued)

OTHER PUBLICATIONS

Gedsa, New Tube Feeding Connectors, Jun. 24, 2014.*
(Continued)

*Primary Examiner* — Nathan R Price
*Assistant Examiner* — Melissa A Snyder
(74) *Attorney, Agent, or Firm* — Baker Botts L.L.P.

(57) ABSTRACT

Adapters for a connector assembly for percutaneous tubing are provided. A male adapter (FIG. 22*a*, 1000) includes a connector fitting (1002) proximate a first end, the connector fitting configured to join to a connector for a tubing system or device, and a male connector (656) proximate a second end. The male connector includes a plug end with a fluid lumen defined therethrough, the plug end having a circum-
(Continued)

ferential groove defined therein to receive a locking extension of a female connector sized to be received within the circumferential groove of the plug end to allow the female connector to rotate relative to and maintain axial engagement with the male connector when the locking extension is received within the groove. An adapter having a female connector (FIG. 24, 1300) is also provided.

16 Claims, 27 Drawing Sheets

(51) Int. Cl.
    *A61M 39/02*     (2006.01)
    *A61M 5/142*     (2006.01)
    *A61M 39/20*     (2006.01)
    *A61M 25/02*     (2006.01)

(52) U.S. Cl.
    CPC ....... *A61J 15/0069* (2013.01); *A61J 15/0073* (2013.01); *A61J 15/0076* (2015.05); *A61J 15/0092* (2013.01); *A61M 5/142* (2013.01); *A61M 39/0247* (2013.01); *A61M 39/105* (2013.01); *A61M 39/1011* (2013.01); *A61M 39/1055* (2013.01); *A61M 39/20* (2013.01); *A61M 2025/0213* (2013.01); *A61M 2025/0293* (2013.01); *A61M 2039/027* (2013.01); *A61M 2039/0255* (2013.01); *A61M 2039/0273* (2013.01); *A61M 2039/0282* (2013.01); *A61M 2039/0288* (2013.01); *A61M 2039/1016* (2013.01); *A61M 2039/1077* (2013.01); *A61M 2207/00* (2013.01)

(58) Field of Classification Search
    CPC ............ A61J 15/0092; A61M 39/1011; A61M 2039/1094; A61M 2039/0255; A61M 39/00
    See application file for complete search history.

(56) References Cited

U.S. PATENT DOCUMENTS

| | | |
|---|---|---|
| 5,507,535 A | 4/1996 | McKamey et al. |
| 5,549,583 A | 8/1996 | Sanford et al. |
| 5,688,254 A * | 11/1997 | Lopez ................ A61M 39/1011 604/529 |
| 2001/0024778 A1 | 9/2001 | Hoffman |
| 2003/0225369 A1 | 12/2003 | McMichael et al. |
| 2006/0033331 A1 | 2/2006 | Ziman |
| 2006/0129092 A1 | 6/2006 | Hanlon et al. |
| 2006/0270993 A1 | 11/2006 | McMichael et al. |
| 2007/0169825 A1 | 7/2007 | Packham et al. |
| 2008/0140020 A1 * | 6/2008 | Shirley ................. A61M 39/10 604/240 |
| 2009/0259211 A1 * | 10/2009 | Yanuma ............ A61M 25/1018 604/509 |
| 2011/0190733 A1 | 8/2011 | D'Lima et al. |
| 2012/0029483 A1 * | 2/2012 | Griffith ............... A61J 15/0015 604/535 |
| 2012/0053525 A1 | 3/2012 | Delegge et al. |
| 2013/0046287 A1 * | 2/2013 | Davis .................... A61M 39/10 604/535 |
| 2016/0206516 A1 * | 7/2016 | Kunishige .......... A61J 15/0026 |

FOREIGN PATENT DOCUMENTS

| | | |
|---|---|---|
| EP | 0 616 817 A1 | 9/1994 |
| EP | 1 479 405 A1 | 11/2004 |
| EP | 2 881 138 A1 | 6/2015 |
| JP | 07100213 A | 4/1995 |
| JP | 2001-346887 A | 12/2001 |
| JP | 2004-201904 A | 7/2004 |
| JP | 2004-344281 A | 12/2004 |
| JP | 2005-525154 A | 8/2005 |
| JP | 2013-252165 A | 12/2013 |
| KR | 10-2014-0051726 A | 5/2014 |
| WO | WO 2008/035422 A1 | 3/2008 |
| WO | WO 2009/083835 A1 | 7/2009 |
| WO | WO 2011/097129 A1 | 8/2011 |
| WO | WO 2014/021390 A1 | 2/2014 |

OTHER PUBLICATIONS

ISO 80369-1. First edition, Jul. 1, 2016. p. 1.*
U.S. Appl. No. 15/401,458 (US 2017/0156987), filed Jan. 9, 2017 (Jun. 8, 2017).
International Search Report dated Nov. 13, 2014 in International Application No. PCT/US2014/046229.
International Search Report dated Oct. 21, 2015 in International Application No. PCT/US2015/040001.
U.S. Appl. No. 15/401,458, Apr. 17, 2020 Notice of Allowance.
U.S. Appl. No. 15/401,458, Oct. 1, 2019 Non-Final Office Action.

* cited by examiner

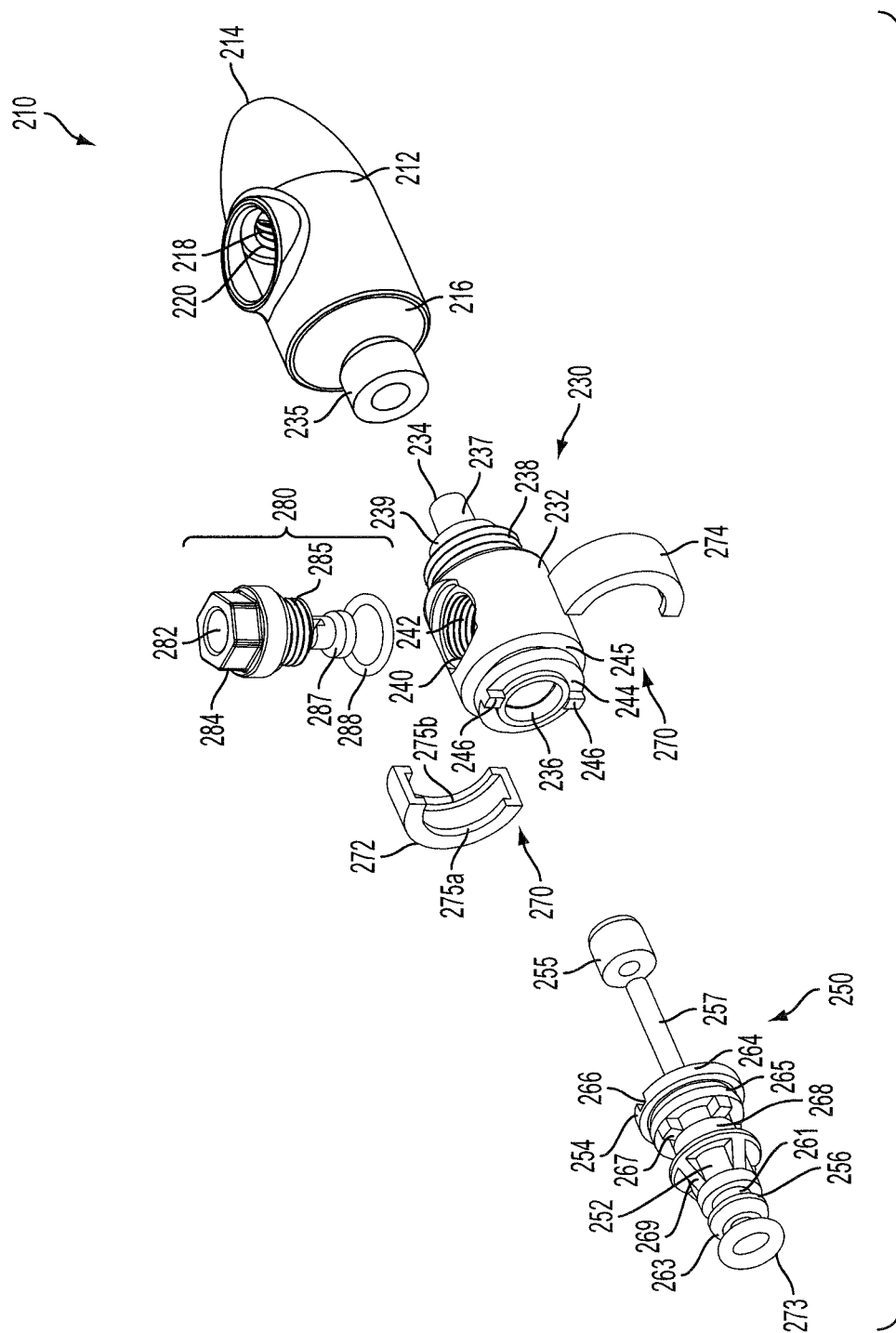

SYSTEMS AND METHODS FOR TUBING DELIVERY

CROSS-REFERENCE TO RELATED APPLICATIONS

This application claims priority to International Patent Application Ser. No. PCT/US2014/046229, filed Jul. 10, 2014, which is incorporated by reference herein in its entirety.

RELATED APPLICATION

This application claims priority from PCT application serial number PCT/US2014/046229, filed Jul. 10, 2014, and PCT application serial number PCT/US2015/040001, filed Jul. 10, 2015, the entireties of all of which are incorporated herein by reference

BACKGROUND

Field of the Disclosed Subject Matter

The present disclosed subject matter relates to delivery tube assemblies, including systems and techniques for disposing percutaneous tubing in a patient.

Description of Related Art

Certain delivery tube assemblies are known and used in the medical arts, including for enteral and parenteral indications. For example, percutaneous endoscopic gastrostomy (PEG) is an endoscopic medical procedure in which a tube ("PEG tube" or "G-tube") is positioned into a patient's gastrointestinal system, such as the stomach, through the abdominal wall. A PEG tube can be utilized to treat or feed a patient when oral intake is not adequate (for example, because of dysphagia or sedation). The PEG tube can also be utilized to administer medication therethrough, for example when beneficial absorption of the medication is not adequate by oral administration. The tubing system can also be extended further into the gastrointestinal system, such as the small intestine, by passing a jejunal extension tube ("PEG-J tube" or "J-tube") through the PEG tube and into the jejunum via the pylorus, for example to bypass the stomach to administer medication directly to the jejunum.

PEG can involve puncturing the abdominal wall, creating a stoma, and feeding the G-tube therethrough and into the stomach. The J-tube can be fed through the G-tube and through the stomach and duodenum into the jejunum. An internal bumper can be placed inside the stomach and attached about the G-tube, for example to prevent or inhibit the G-tube from migrating out from the stoma.

A tubing system can include an external bumper secured to the G-tube and placed on or near the skin proximate the stoma, for example to protect the stoma and guide the G-tube and J-tube exiting the stoma. The external bumper can also prevent or inhibit the external portion of the G-tube and J-tube migrating into the stomach through the stoma. Additionally or alternatively, the tubing system can include a patient-side connector attached to an end of the external portion of the G-tube and J-tube, for example to facilitate attachment of the G-tube and J-tube to an external device, such as a food or medication delivery device. The patient-side connector can also facilitate flushing of the G-tube and J-tube, including separate flushing of each tube.

However, there remains a need for further improvement of known percutaneous tubing systems, such as PEG-J tubing systems. For example, it can be desirable for a connector to provide a simple connection to an external device, while also preventing or inhibiting accidental disconnect and/or dislocation of the J-tube. Also, it can be desirable for a bumper to allow for flexible movement and rotation of the G-tube and J-tube. It can further be desirable for the bumper to guide the G-tube and J-tube out of the stoma substantially perpendicular to the stomach, for example to promote proper stoma healing, while also allowing the G-tube and J-tube to lie substantially flat, in parallel with the abdomen, which can decrease the visibility of the tube. In addition, it can be desirable for the tubing system to include one or more adapters, for example, to provide connectivity between the tubing system described herein and other tubing systems or devices, including conventional connections for such tubing systems or devices. The tubing systems and methods according to the disclosed subject matter can provide these and other advantages.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a male adapter for a connector assembly for percutaneous tubing, the male adapter having a first end and a second end and generally including a connector fitting proximate the first end and a male connector proximate the second end. The connector fitting is configured to join to a connector for a tubing system or device. The male connector includes a plug end with a fluid lumen defined therethrough, the plug end having a circumferential groove defined therein to receive a locking extension of a female connector sized to be received within the circumferential groove of the plug end to allow the female connector to rotate relative to and maintain axial engagement with the male connector when the locking extension is received within the circumferential groove.

Additionally, and as embodied herein, the connector fitting can be configured to join to a standard connector. Alternatively, the connector fitting can be configured to join to a non-standard connector.

Furthermore, and as embodied herein, the connector fitting can include a female ENFit connector. Alternatively, the connector fitting can include a Luer connector. For example, and as embodied herein, the connector fitting can include a female reverse Luer connector.

In addition, and as embodied herein, the male adapter can include a peripheral flange disposed between the first end and the second end. The peripheral flange can be clover shaped.

According to other aspects of the disclosed subject matter, a female adapter for a connector assembly for percutaneous tubing is provided. The female adapter has a first end and a second end and generally includes a connector fitting proximate the first end and a female connector proximate the second end. The connector fitting is configured to join to a connector for a tubing system or device. The female connector includes a lever having a locking extension, the locking extension sized to be received within a groove defined in a male plug end of a male connector to allow the female connector rotate relative to and maintain axial engagement with the male connector when the locking extension is received within the groove.

Additionally, and as embodied herein, the connector fitting can be configured to join to a standard connector. Alternatively, the connector fitting can be configured to join to a non-standard connector.

Furthermore, and as embodied herein, the connector fitting can include an ENFit connector. Alternatively, the connector fitting can include a Luer connector. As embodied herein, the connector fitting can include a male reverse Luer connector. The connector fitting can be configured to receive a syringe to flush the inner J-tube of the percutaneous tubing system when joined to the female connector.

According to other aspects of the disclosed subject matter, a connector kit for percutaneous tubing is provided. The kit generally includes a female connector and a male adapter. The female connector has a first end and a second end and includes a lever having a locking extension proximate the first end. The female connector is configured to be joined to a fluid source proximate the second end. The male adapter has a first end and a second end and includes a connector fitting proximate the first end, the connector fitting configured to join to a connector for a percutaneous tubing system. The male adapter also includes a male connector proximate the second end, the male connector including a plug end with a fluid lumen defined therethrough. The plug end has a circumferential groove defined therein to receive the locking extension of the female connector to allow the female connector to rotate relative to and maintain axial engagement with the male connector when the locking extension is received within the circumferential groove. The female connector and the male adapter can include any combination of features described herein.

According to other aspects of the disclosed subject matter, a connector kit for percutaneous tubing is provided. The percutaneous tubing includes an outer G-tube and an inner J-tube. The kit generally includes a male connector and a female adapter. The male connector includes a shell having a sidewall defining an interior, a first shell end having a first opening defined therein, and a second shell end having a second opening defined therein, each of the first and second openings in communication with the interior to receive the percutaneous tubing therethrough, the shell further having an engagement portion, a connector body having a first body end and a second body end with a tube lumen defined therethrough, the first body end having a connector tip sized to receive the inner J-tube therethrough and mate with the outer G-tube, the connector body having an engaging portion to engage the engagement portion of the shell, and a plug configured to be joined to the connector body and having a first plug end and a second plug end with a fluid lumen defined therethrough, the first plug end having a plug tip extending therefrom, the tip sized to mate with the inner J-tube. The female adapter has a first end and a second end and includes a connector fitting proximate the first end, the connector fitting configured to join to a connector for a fluid source. The female adapter also includes a female connector proximate the second end, the female connector comprising a lever having a locking extension, the locking extension sized to be received within the groove defined in the second plug end of the male connector to allow the female connector to rotate relative to and maintain axial engagement with the male connector when the locking extension is received within the groove. The male connector and the female adapter can include any combination of features described herein.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE DRAWINGS

FIG. 4A is an exploded top perspective view of the exemplary male connector assembly of FIG. 3A.

DETAILED DESCRIPTION OF THE PREFERRED EMBODIMENT

Figure 1:
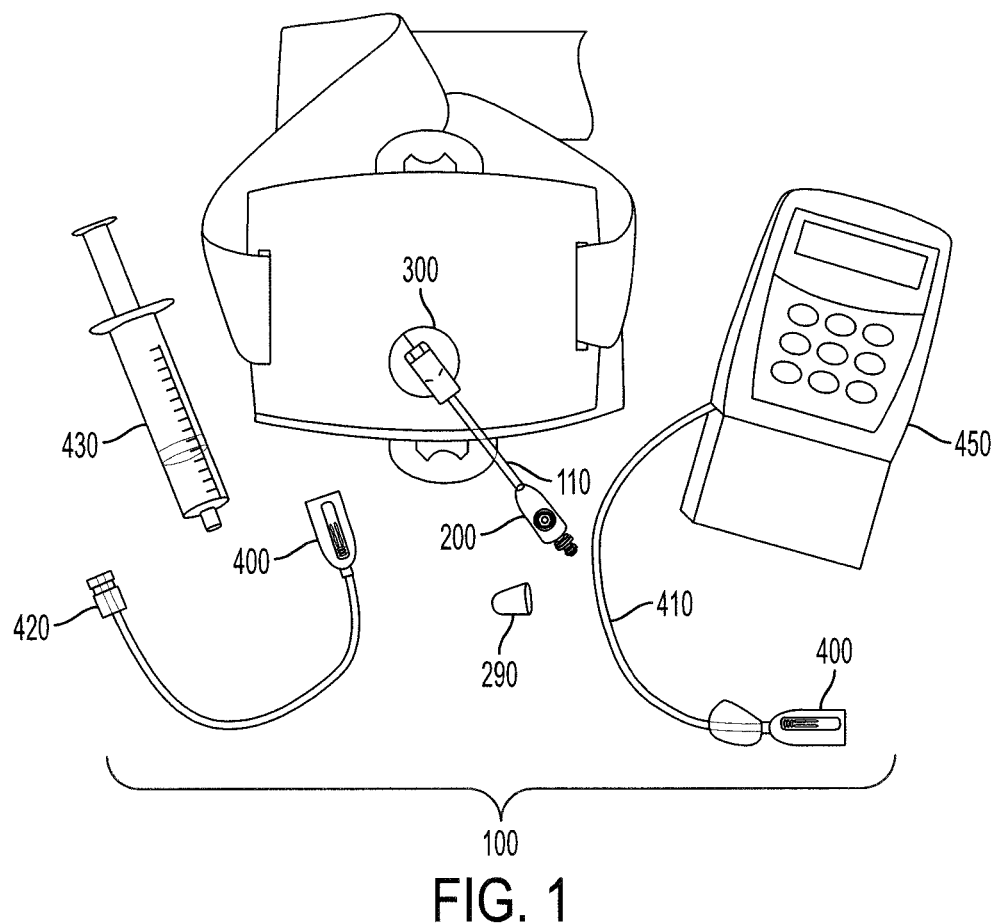
FIG. 1 is a plan view of an exemplary tubing system, including an exemplary male connector assembly according to an illustrative embodiment of the disclosed subject matter.

Reference will now be made in detail to the various exemplary embodiments of the disclosed subject matter, exemplary embodiments of which are illustrated in the accompanying drawings. The structure and corresponding method of operation of and method of treatment using the disclosed subject matter will be described in conjunction with the detailed description of the system.

The apparatus and methods presented herein can be used for administering any of a variety of suitable therapeutic agents or substances, such as a drug or biologic agent, to a patient. For example, and as embodied herein, the tubing system can be joined to a therapeutic agent delivery device, such as a pump, to deliver a therapeutic agent through the tubing system. As used herein, a "therapeutic agent delivery device" or "delivery device" (used interchangeably herein) is intended to refer generally to a device capable of administering a dosage of a fluid substance, such as a therapeutic agent, including a formulation in a liquid or gel form, through the tubing system and to a patient. In some embodiments, the fluid therapeutic agent can include one or more pharmaceutical or biologic agents. For example and without limitation, one such fluid therapeutic agent can be a central nervous system agent, such as levodopa. The central nervous system agent can be administered alone or in combination with, for example and without limitation, a decarboxylase inhibitor, such as carbidopa.

In accordance with the disclosed subject matter herein, a connector assembly for percutaneous tubing including an outer tube, such as a G-tube, and an inner tube, such as a J-tube, is provided. The connector assembly generally includes a male connector assembly having a shell, a connector body and a plug. The shell has a sidewall defining an interior, a first shell end having a first opening defined therein, and a second shell end having a second opening defined therein, each of the first and second openings in communication with the interior to receive the percutaneous tubing therethrough, the shell further having an engagement portion. The connector body has a first body end and a second body end with a tube lumen defined therethrough, the first body end having a connector tip sized to receive the inner J-tube therethrough and mate with the outer G-tube, the connector body having an engaging portion to engage the engagement portion of the shell. The plug is joined to the connector body and has a first plug end and a second plug end with a fluid lumen defined therethrough, the first plug end having a plug tip extending therefrom, the tip sized to mate with the inner J-tube.

The accompanying figures, where like reference numerals refer to identical or functionally similar elements throughout the separate views, serve to further illustrate various embodiments and to explain various principles and advantages all in accordance with the disclosed subject matter. For purpose of explanation and illustration, and not limitation, exemplary embodiments of the tubing assembly and related components in accordance with the disclosed subject matter are shown in FIGS. 1-24H. While the present disclosed subject matter is described with respect to using the tubing system with a delivery device to administer a dose of therapeutic agent, one skilled in the art will recognize that the disclosed subject matter is not limited to the illustrative embodiment, and that the connector assembly can be a component of any suitable tubing system for delivering any suitable substance therethrough. In addition, the components and the method of using the connector assembly are not limited to the illustrative embodiments described or depicted herein. For example, the bumper embodied herein can be used with other tubing assemblies for similar benefits and advantages. Likewise, the connector assembly can be configured for use with other device connectors, including conventional adapters, as shown for purpose of illustration and not limitation in FIGS. 22A-24H, and not be limited for use with the device connectors herein.

Figure 5:
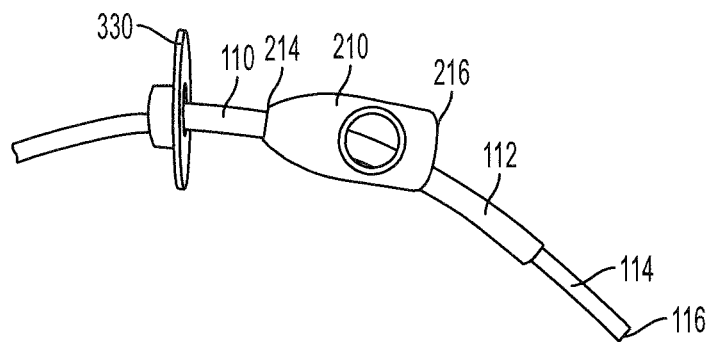
FIG. 5 is a perspective view of percutaneous tubing inserted through an exemplary shell according to the disclosed subject matter.

Referring to an illustrative embodiment of FIG. 1, a tubing system 100 includes a percutaneous tubing 110 having an outer G-tube 112 and an inner J-tube 114 extending therethrough, as shown for example in FIG. 5. With reference to FIG. 1, an end of the percutaneous tubing 110 external to the patient can have a connector assembly 200 joined thereto, which can be configured, for example and as embodied herein, as a male connector assembly. As described further below, the tubing system 100 embodied herein includes a bumper 300 disposed about the percutaneous tubing 110 spaced a distance from the connector assembly 200. As described further below, the connector assembly 200 is configured to join to a device connector 400, which can be configured, for example and as embodied herein, as a female connector. The device connector 400 is coupled with a delivery device or fluid source, and thus joins the percutaneous tubing 110 to such delivery device or fluid source. For example, as shown in FIG. 1, a fluid source connector 420 can be coupled with device connector 400 via tubing 410. Fluid source connector 420 can be configured, for example and without limitation, as an oral/enteral connector, luer connector, or any other suitable fluid-tight connector and can be used, for example and without limitation, to join to a fluid source, such as syringe 430 to dispense fluid through the percutaneous tubing 110. Additionally or alternatively, as shown in FIG. 1, a pump device 450 can be coupled with device connector 400 via tubing 410, and the pump device 450 can be used, for example and without limitation, to pump a fluid through the percutaneous tubing 110.

Figure 2:
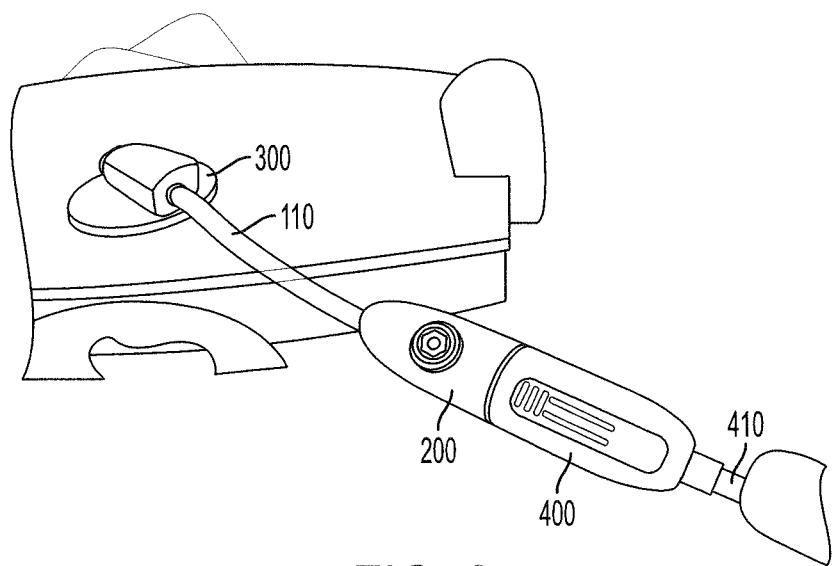
FIG. 2 is a perspective view of the exemplary tubing system of FIG. 1, with the male connector assembly joined to a female connector.
Figure 3A:
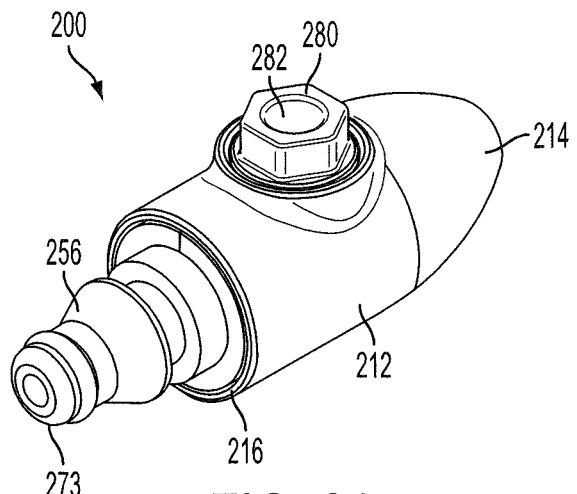
FIG. 3A is a top perspective view of the exemplary male connector assembly of the exemplary tubing system of FIG. 1.
Figure 3B:
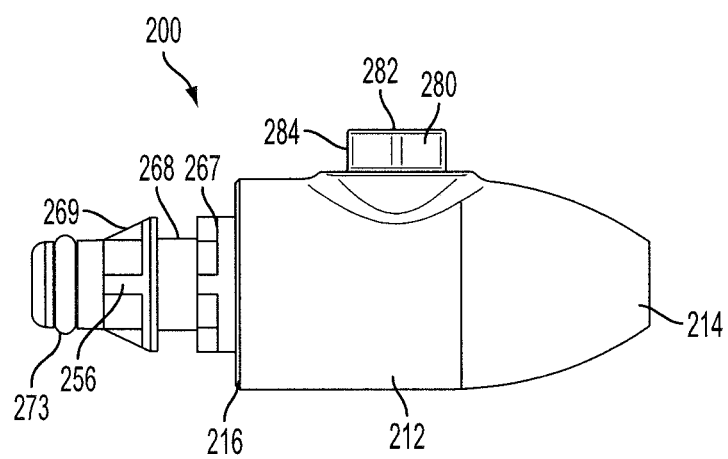
FIG. 3B is a side view of the exemplary male connector assembly of FIG. 3A.
Figure 3C:
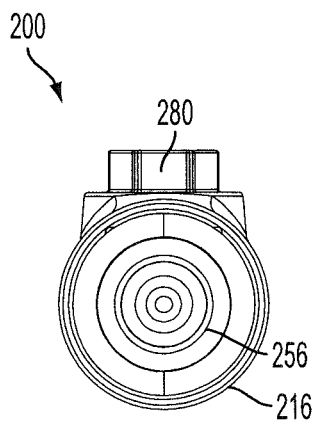
FIG. 3C is a front view of the exemplary male connector assembly of FIG. 3A.
Figure 3D:
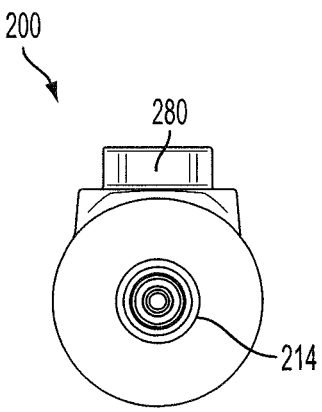
FIG. 3D is a rear view of the exemplary male connector assembly of FIG. 3A.

With reference now to FIG. 2, percutaneous tubing 110 is illustrated with connector assembly 200 joined thereto. Connector assembly 200 is joined in line with device connector 400, which can be joined to any device or fluid source as described herein. As described further below, bumper 300 is disposed on or near the skin of a patient proximate a stoma, and percutaneous tubing 110 extends through bumper 300 and the stoma into the stomach.

With reference to FIGS. 3A-4C, an exemplary connector assembly 200 is illustrated. As shown for example in FIGS. 4A-4C, the connector assembly 200 generally includes a shell 210, a connector body 230, a plug 250 and a clip 270. The shell has a sidewall 212 defining an interior. As embodied herein, the shell has a first shell end 214 with a first opening defined therein, and a second shell end 216 with a second opening defined therein. The openings in the first and second shell ends 214, 216 are in communication with the interior to receive the percutaneous tubing 110 therethrough.

Figure 4B:
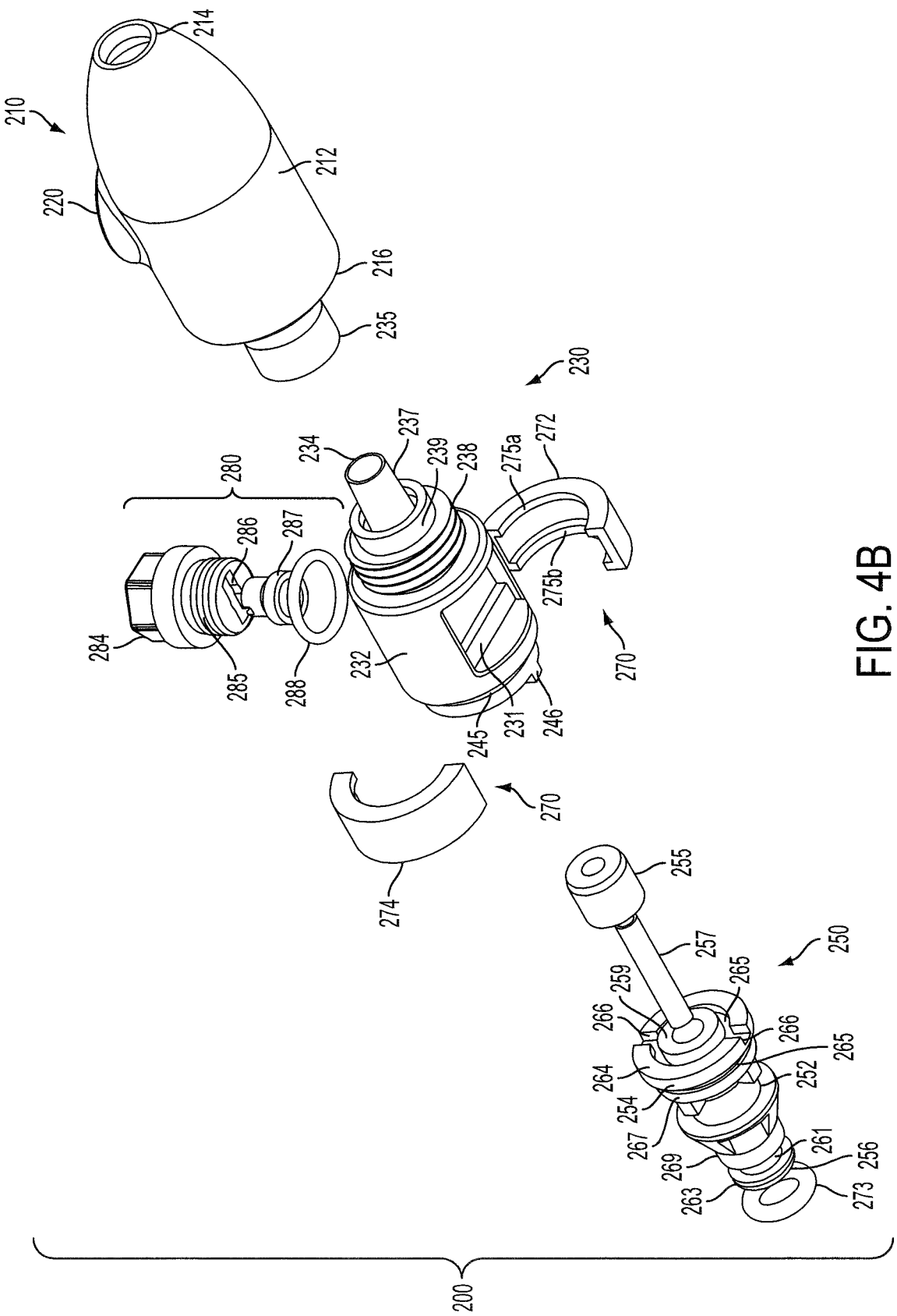
FIG. 4B is an exploded bottom perspective view of the exemplary male connector assembly of FIG. 3A.
Figure 4C:
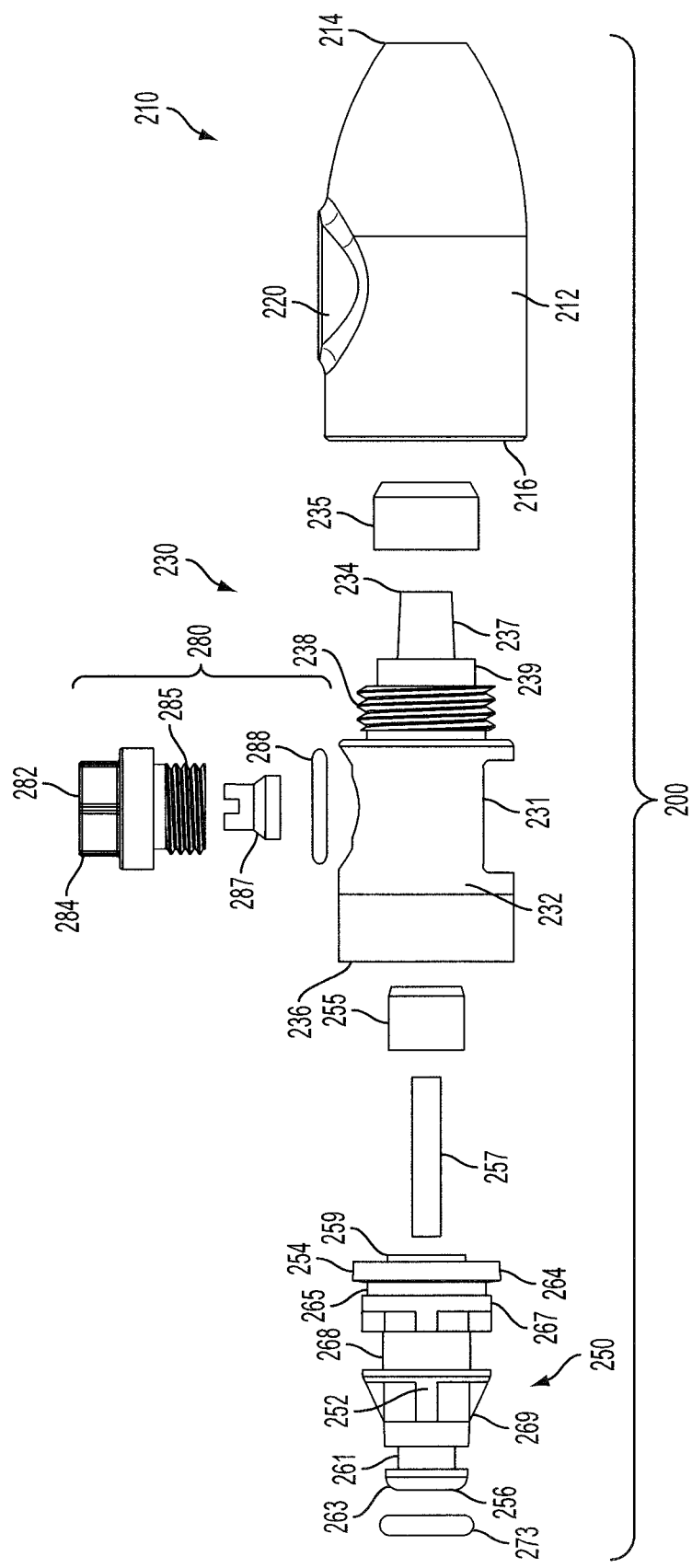
FIG. 4C is an exploded side view of the exemplary male connector assembly of FIG. 3A.

With reference to FIGS. 4A-4C, the shell further has an engagement portion 218. As embodied herein, the engagement portion 218 can be configured as a threaded engagement. However, any suitable engagement configuration can be used, for example and without limitation, a snap-fit engagement, a latch engagement or any other suitable engagement. Furthermore, and as embodied herein, the engagement portion 218 can be disposed within the interior of the shell 210.

Furthermore, and as embodied herein, the sidewall 212 of the shell 210 can have an aperture 220 defined therein. The aperture 220 can allow access to the interior of the shell 210 through the sidewall 212. For example and as embodied herein, the aperture 220 can be sized to receive a valve 280, or other suitable fluid regulating component, to allow selective fluid access to the interior of the shell 210 through the aperture 220, as discussed further herein.

Referring to FIGS. 4A-4C, connector assembly 200 includes a connector body 230. As embodied herein, the connector body 230 has a sidewall 232 defining a first body end 234 and a second body end 236 with a tube lumen defined therethrough. The first body end 234 has a connector tip 237. As embodied herein, connector tip 237 has an inner diameter sized to receive the inner J-tube 114 therethrough. Additionally, and as embodied herein, connector tip 237 has an outer diameter sized to mate with the outer G-tube 112. In addition, in some embodiments, the connector tip 237 can be tapered. Alternatively, the connector tip 237 can have a uniform cross-dimension. Furthermore, connector body 230 can include a recessed portion 231 formed in the sidewall 232 thereof. Recessed portion 231 can provide a structure having improved moldability, for example by reducing the amount of surface area susceptible to surface depressions.

As embodied herein, the connector assembly 200 can also include a ferrule 235 sized to receive the G-tube 112 therethrough. Furthermore, and as embodied herein, the connector body 230 can include a rim 239 surrounding the connector tip 237. The G-tube 112 can thus extend through the connector body 230 between the connector tip 237 and the rim 239. The ferrule 235 can thus be sized to be disposed over the connector tip 237 to engage the connector body 230 and cover the G-tube 112 entering the connector body 230. In this manner, ferrule 235 can radially compress G-tube 112 into engagement with connector tip 237. With connector body 230 inserted into shell 210, as described herein, first shell end 214 can provide additional compression to ferrule 235 to further urge G-tube 112 into engagement with connector tip 237.

For example, and as embodied herein, the connector body 230 has an engaging portion 238 to engage the engagement portion 218 of the shell 210. As embodied herein, the engaging portion 238 can be configured as a threaded engagement. However, any suitable engagement configuration can be used for the engaging portion 238 to complement the engagement portion 218 of the shell 210, for example and without limitation, a snap-fit engagement, a latch engagement or any other suitable engagement. Furthermore, and as embodied herein, the engaging portion 238 can be spaced inward from the connector tip 237 along the connector body 230.

Furthermore, and as embodied herein, the sidewall 232 of the connector body 230 can have an aperture 240 defined therein. The aperture 240 can allow access to the interior of the connector body 230 through the sidewall 232. For example and as embodied herein, the aperture 240 can be sized to receive a valve 280, or other suitable fluid regulating component, to allow selective fluid access to the interior of the connector body 230 through the aperture 240, as discussed further herein. Additionally, the connector body 230 can have an engagement portion 242 proximate aperture 240, for example to engage valve 280 to the connector body 230. For example, and as embodied herein, engagement portion 242 can be a threaded engagement. However, any suitable engagement can be used, for example and without limitation, a snap-fit engagement, a latch engagement or any other suitable engagement.

Additionally, and as embodied herein, the second body end 236 can include a flange 244 surrounding the second body end 236 aperture and defining a groove 245 between the flange 244 and the sidewall 232. The flange 244 and groove 245 can form a portion of a fastener for the connector body 230, as described further herein. Furthermore, as embodied herein, the flange 244 can include projections 246 projecting therefrom, which can match corresponding receptacles to secure the connector body 230 in proper rotational alignment with a component attached at the second body end 236, as described further herein.

With continued reference to FIGS. 4A-4C, as embodied herein, the connector assembly 200 includes a plug 250. Plug 250 has a plug body 252 defining a first plug end 254 and a second plug end 256 with a fluid lumen defined therethrough. The first plug end 254 has a plug tip 257 extending therefrom. As embodied herein, the plug tip 257 is sized to mate with the inner J-tube 114. For example, as embodied herein, the plug tip 257 defines a lumen with an outer diameter sized to fit within the J-tube 114, and can be formed as a stainless steel tube or a molded plastic tube. The first plug end 254 can have a rim 259 sized to receive the plug tip 257 therein. As embodied herein. the connector assembly 200 can also include a ferrule 255 sized to receive the plug tip 257 and be received within and engage the second body end 236 of the connector body 230. The ferrule 255 can thus be sized to be disposed over the plug tip 257 to engage the connector body 230 and cover the J-tube 114 entering the connector body 230. In this manner, ferrule 255 can radially compress J-tube 114 into engagement with plug tip 257.

Additionally, and as embodied herein, the second plug end 256 can include a flange 264 surrounding the second plug end 256 aperture and defining a groove 265 between the flange 264 and the sidewall 252. The flange 264 and groove 265 can form a portion of a fastener to fasten the plug 250 to the connector body 230. For example, as embodied herein, flange 264 can have a size similar to flange 244. Furthermore, as embodied herein, the flange 264 can define recesses 266 to receive projections 246 of the connector body 230 to engage the plug 250 thereto in proper rotational alignment.

As previously noted, a fastener can be provided to join the connector body 230 to the plug 250. The fastener can be formed integral with the connector body 230 and/or the plug 250. For example, the fastener can be a threated configuration, a snap fit, or the like. With reference to FIGS. 4A-4C, and as embodied herein, the fastener can include a clip 270. For example, clip 270 can have notches 275a, 275b configured to be disposed within groove 245 of the connector body 230 and groove 265 of the plug 250 to secure the plug 250 to the connector body 230. As embodied herein, the clip 270 can be configured as two semicircular clip portions 272, 274, each configured to be disposed within the grooves 245, 265 to form the clip 270. In some embodiments, the two clip portions 272, 274 can be hingedly joined to each other at an end of each clip portion 272, 274. Alternatively, clip 270 can be configured as a single piece component.

Furthermore, and as embodied herein, the second plug end 256 can define a connector to couple with a device connector 400. The second plug end 256 can include a ring portion 267 and a frustoconical portion 269 defining a groove 268 therebetween. Groove 268 thus can facilitate an engagement between the device connector 400 and the connector assembly 200, as discussed further herein. Additionally, an open plug nub 263 can extend from the frustoconical portion 269 to define a second groove 261 therebetween. Second groove 261 can be sized to receive a gasket 273 to provide a seal between the plug 250 and the device connector 400.

Still with reference to FIGS. 4A-4C, and as embodied herein, the connector assembly 200 can include a valve 280 sized to be disposed within apertures 220 and 240 and in communication with the connector body 230. For example, and as embodied herein, the valve 280 can have an engaging portion 285 to engage the engagement portion 242 of the connector body 230. As embodied herein, the engaging portion 285 can be configured as a threaded engagement. However, any suitable engagement configuration can be used to complement the engagement portion 242 of the connector body 230, for example and without limitation, a snap-fit engagement, a latch engagement or any other suitable engagement. Valve 280 can include a grip portion 284, which can be configured for example as a hexagonal head or any other suitable fastener or driver head, for example to allow the valve 280 to be gripped or turned into or out of engagement with the connector body 230. With reference to FIG. 4B, the valve 280 can include a slot 286 to receive a fitting 287, which can extend from the valve 280 and be disposed within the connector body 230 to secure the valve 280 therein. An o-ring 288 can be disposed about the valve 280 proximate the engaging portion 285 to provide a fluid-tight seal between the valve 280 and the connector body 230. Additional or alternative sealing techniques can be employed.

Furthermore, and as embodied herein, valve 280 can include a port 282 to receive a fluid injecting device, for example and without limitation a syringe 430. For example and without limitation, and as embodied herein, the port 282 can be configured as an oral/enteral connector, luer connector, or any other suitable fluid-tight connector to receive a corresponding syringe. In this manner, fluid can be introduced into the connector body and through the G-tube 112 while bypassing the J-tube 114. This configuration can be utilized, for example, to flush the G-tube 112 with liquid or administer a liquid directly to the stomach through the G-tube 112.

With reference to FIGS. 16A-17C, an alternative embodiment of an exemplary connector assembly 600 is illustrated. As shown for example in FIGS. 17A-17C, the connector assembly 600 generally includes a shell 610, a connector body 630 and a plug 650. The shell has a sidewall 612 defining an interior. As embodied herein, the shell has a first shell end 614 with a first opening defined therein, and a second shell end 616 with a second opening defined therein. The openings in the first and second shell ends 614, 616 are in communication with the interior to receive the percutaneous tubing 110 therethrough.

Figure 17A:
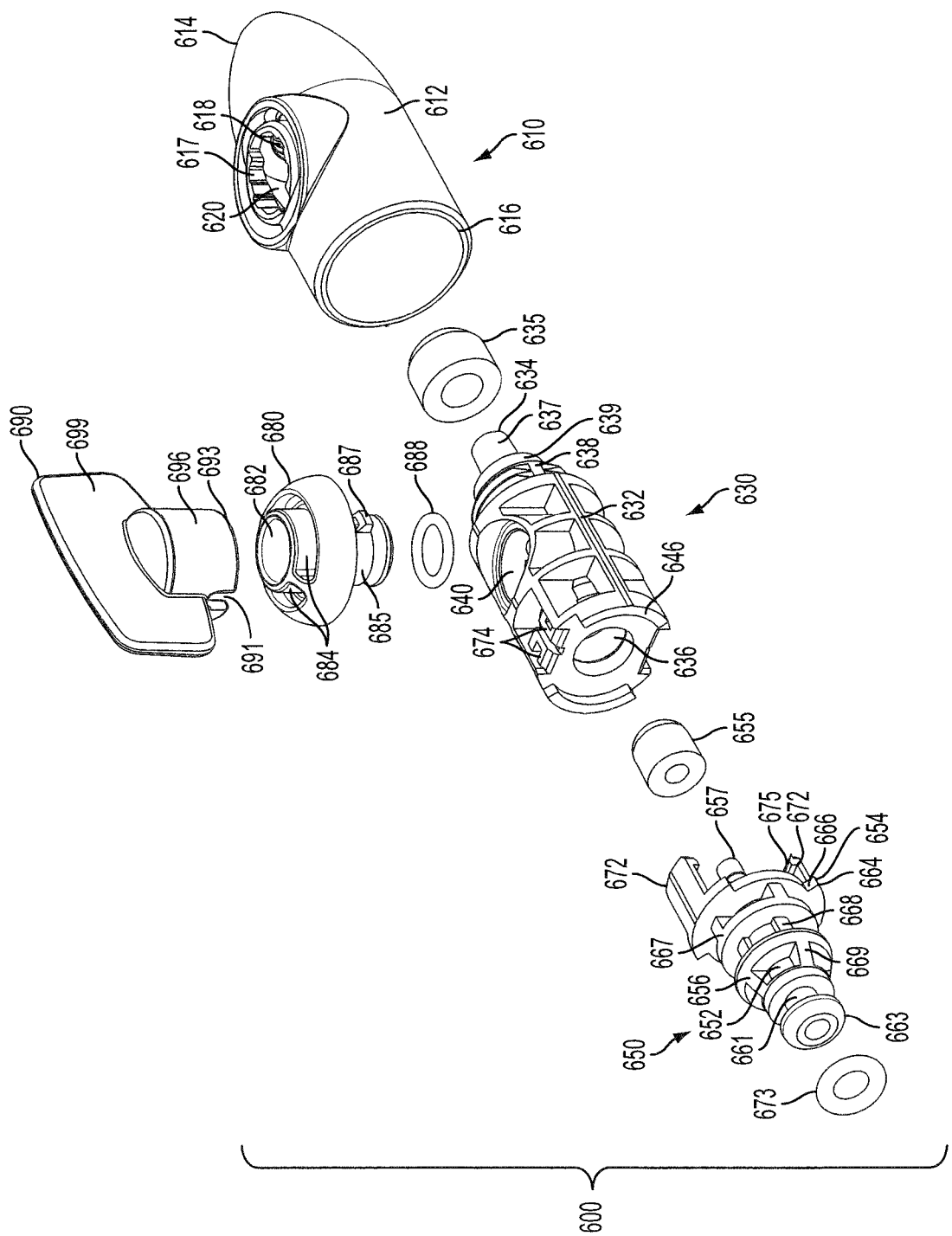
FIG. 17A is an exploded top perspective view of the exemplary male connector assembly of FIG. 16A.
Figure 17B:
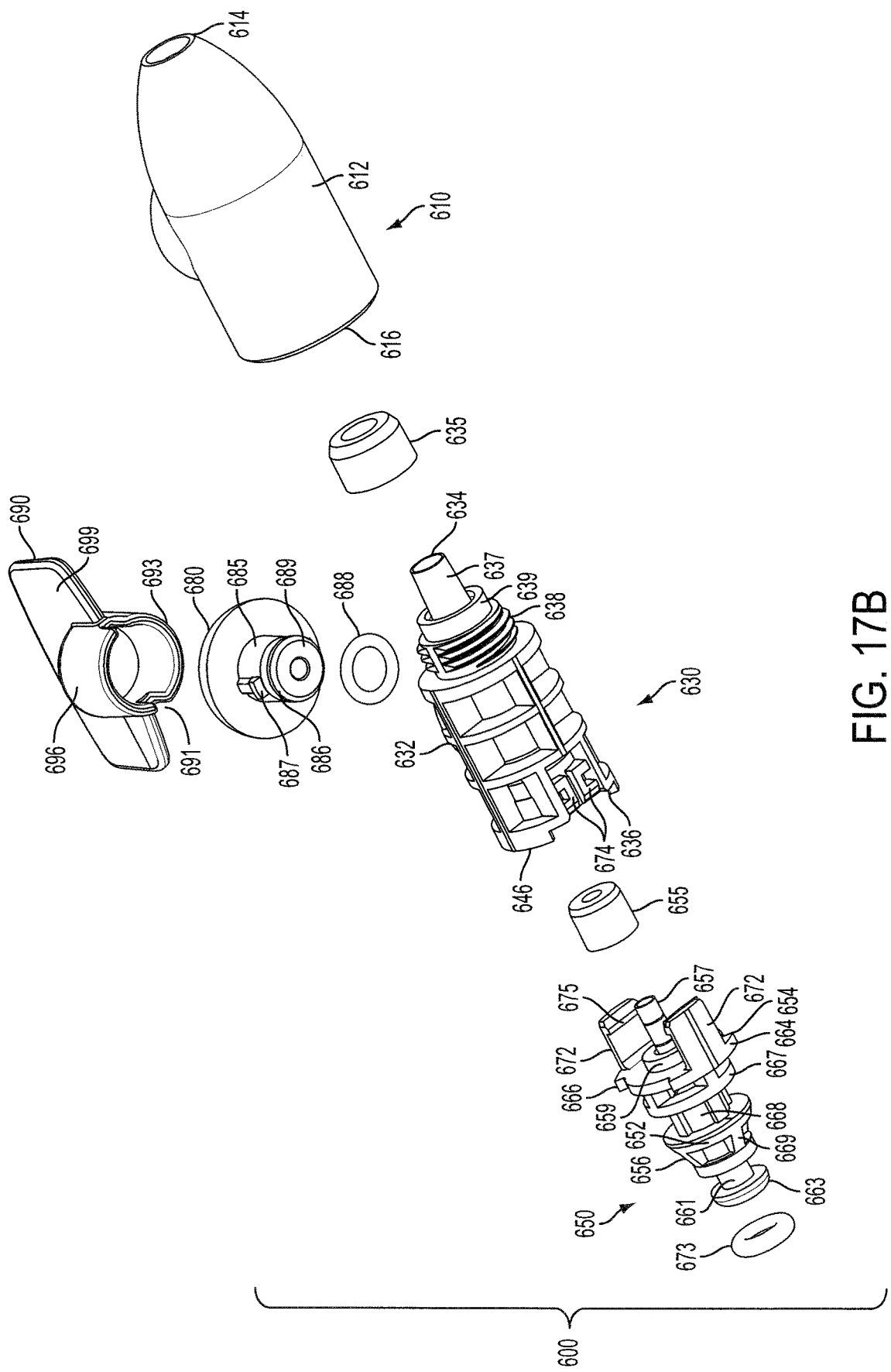
FIG. 17B is an exploded bottom perspective view of the exemplary male connector assembly of FIG. 16A.
Figure 17C:
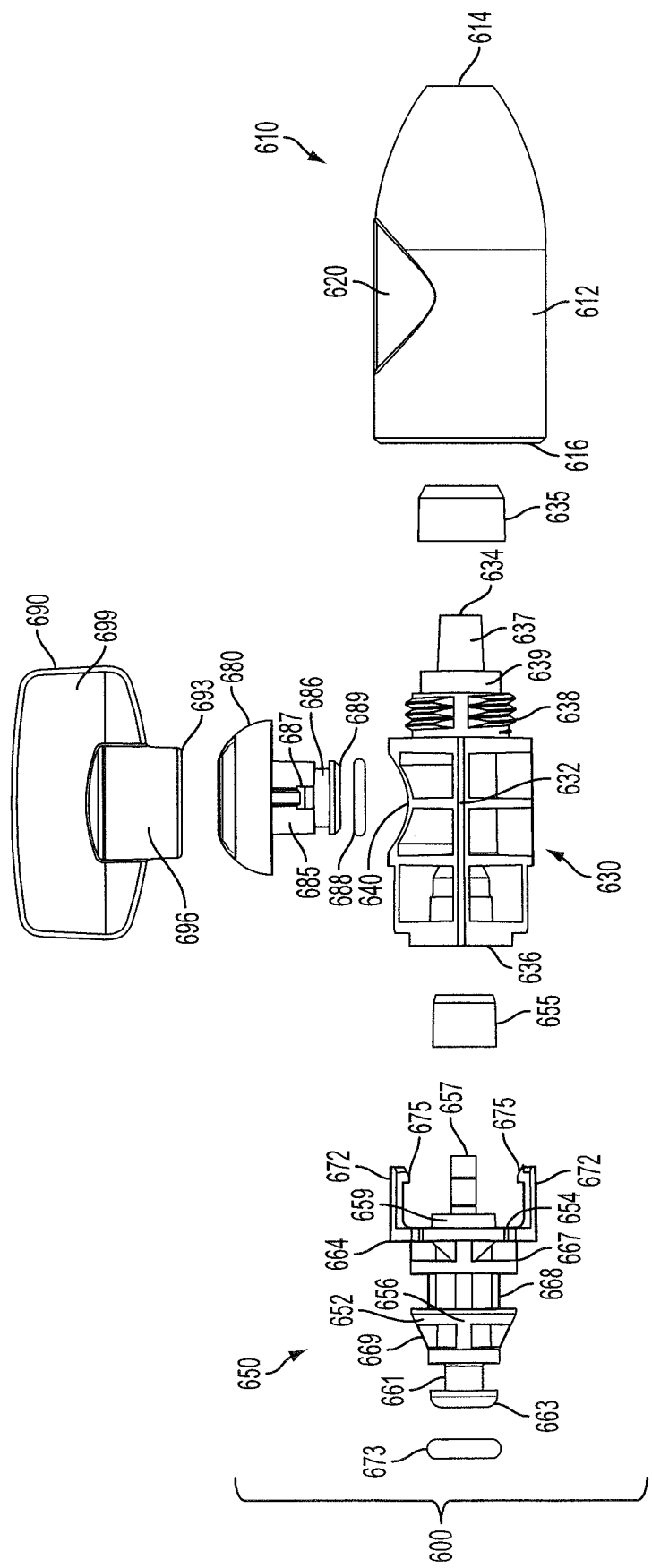
FIG. 17C is an exploded side view of the exemplary male connector assembly of FIG. 16A.

With reference to FIGS. 17A-17C, the shell further has an engagement portion 618. As embodied herein, the engagement portion 618 can be configured as a quarter-turn lock engagement. However, any suitable engagement configuration can be used, for example and without limitation, a snap fit engagement, threaded engagement, a latch engagement or any other suitable engagement. Furthermore, and as embodied herein, the engagement portion 618 can be disposed within the interior of the shell 610.

Furthermore, and as embodied herein, the sidewall 612 of the shell 610 can have an aperture 620 defined therein. The aperture 620 can allow access to the interior of the shell 610 through the sidewall 612. For example and as embodied herein, the aperture 620 can be sized to receive a valve 680, or other suitable fluid regulating component, to allow selective fluid access to the interior of the shell 610 through the aperture 620, as discussed further herein.

Referring to FIGS. 17A-17C, connector assembly 600 includes a connector body 630. As embodied herein, the connector body 630 has a sidewall 632 defining a first body end 634 and a second body end 636 with a tube lumen defined therethrough. The first body end 634 has a connector tip 637. As embodied herein, connector tip 637 has an inner diameter sized to receive the inner J-tube 114 therethrough. Additionally, and as embodied herein, connector tip 637 has an outer diameter sized to mate with the outer G-tube 112. In addition, in some embodiments, the connector tip 637 can be tapered. Alternatively, the connector tip 637 can have a uniform cross-dimension.

As embodied herein, the connector assembly 600 can also include a ferrule 635 sized to receive the G-tube 112 therethrough. Furthermore, and as embodied herein, the connector body 630 can include a rim 639 surrounding the connector tip 637. The G-tube 112 can thus extend through the connector body 630 between the connector tip 637 and the rim 639. Ferrule 635 can thus be sized to be disposed over the connector tip 637 to engage the connector body 630 and cover the G-tube 112 entering the connector body 630. In this manner, ferrule 635 can radially compress G-tube 112 into engagement with connector tip 637. With connector body 630 inserted into shell 610, as described herein, first shell end 614 can provide additional radial compression of ferrule 635 to further compress G-tube 112 into engagement with connector tip 637.

For example, and as embodied herein, the connector body 630 has an engaging portion 638 to engage the engagement portion 618 of the shell 610. As embodied herein, the engaging portion 638 can be configured as a threaded engagement. However, any suitable engagement configuration can be used for the engaging portion 638 to complement the engagement portion 618 of the shell 610, for example and without limitation, a snap-fit engagement, a latch engagement or any other suitable engagement. Furthermore, and as embodied herein, the engaging portion 638 can be spaced inward from the connector tip 637 along the connector body 630.

Furthermore, and as embodied herein, the sidewall 632 of the connector body 630 can have an aperture 640 defined therein. The aperture 640 can allow access to the interior of the connector body 630 through the sidewall 632. For example and as embodied herein, the aperture 640 can be sized to receive a valve 680, or other suitable fluid regulating component, to allow selective fluid access to the interior of the connector body 630 through the aperture 640, as discussed further herein. Additionally, with connector body 630 engaged with shell 610, aperture 620 and aperture 640 can be aligned. Furthermore, shell 610 can have an engagement portion 617 proximate aperture 620, for example to engage valve 680 to shell 610 in fluid communication with connector body 630. For example, and as embodied herein, engagement portion 617 can be a molded component keyed to valve body 685 and locking finger 687 to provide a quarter-turn lock engagement. However, any suitable engagement can be used, for example and without limitation, a threaded engagement, a snap-fit engagement, a latch engagement or any other suitable engagement.

As embodied herein, connector body 630 can include one or more flange portions 646 proximate second body end 636. Flange portions 646 can be sized to engage a corresponding portion of plug body 652 to join connector body 630 to plug 650. Additionally or alternatively, as embodied herein, connector body 630 can include one or more locking surfaces 674, which can be sized to engage one or more locking projections 672 of plug 650, as discussed further herein.

With continued reference to FIGS. 17A-17C, as embodied herein, the connector assembly 600 includes a plug 650. Plug 650 has a plug body 652 defining a first plug end 654 and a second plug end 656 with a fluid lumen defined therethrough. The first plug end 654 has a plug tip 657 extending therefrom. As embodied herein, the plug tip 657 is sized to mate with the inner J-tube 114. For example, as embodied herein, the plug tip 657 defines a lumen with an outer diameter sized to fit within the J-tube 114, and can be formed as a stainless steel tube or a molded plastic tube. The first plug end 654 can have a rim 659 sized to receive the plug tip 657 therein. As embodied herein, the connector assembly 600 can also include a ferrule 655 sized to receive the plug tip 657 and be received within and engage the second body end 636 of the connector body 630. Ferrule 655 can thus be sized to be disposed over the plug tip 657 to engage the connector body 630 and cover the J-tube 114 entering the connector body 630. In this manner, ferrule 655 can radially compress J-tube 114 into engagement with plug tip 657.

Additionally, and as embodied herein, the second plug end 656 can include a flange 664 surrounding the second plug end 656 aperture and having one or more locking projections 672 extending therefrom. Locking projections 672 can have one or more locking ribs 675 defined therein and can form a portion of a fastener to fasten the plug 650 to the connector body 630. For example, as embodied herein, locking projections 672 and locking ribs 675 can be sized to be received within and engage locking surfaces 674. Furthermore, as embodied herein, the flange 664 can define recesses 666 to receive projections 646 of the connector body 630 to engage the plug 650 thereto in proper rotational alignment. In this manner, a fastener can be provided to join the connector body 630 to the plug 650 that can be formed integral with the connector body 630 and/or the plug 650.

Furthermore, and as embodied herein, the second plug end 656 can define a connector to couple with a device connector 400. The second plug end 656 can include a ring portion 667 and a frustoconical portion 669 defining a groove 668 therebetween. Groove 668 thus can facilitate an engagement between the device connector 400 and the connector assembly 200, as discussed further herein. Additionally, an open plug nub 663 can extend from the frustoconical portion 669 to define a second groove 661 therebetween. Second groove 661 can be sized to receive a gasket 673 to provide a seal between the plug 650 and the device connector 400.

Still with reference to FIGS. 17A-17C, and as embodied herein, the connector assembly 600 can include a valve 680 sized to be disposed within apertures 620 and 640 and in communication with the connector body 630. For example, and as embodied herein, valve 680 can include a valve body 685 with a locking finger 687 to form a press-fit engagement with engagement portion 617 of shell 610. However, any suitable engagement configuration can be used to complement the engagement portion 617 of the shell 610, for example and without limitation, a snap-fit engagement, a latch engagement or any other suitable engagement. Additionally or alternatively, and as embodied herein, valve 680 can engage connector body 630, for example in a press-fit engagement, snap-fit engagement, latch engagement or any other suitable engagement. With reference to FIG. 17A, valve body 685 can include a slot 686 to receive an o-ring 688, which can provide a fluid-tight seal between valve 680 and shell 610. Additional or alternative sealing techniques can be employed. In addition, and as embodied herein, engagement of valve 680 with shell 610 and connector body 630 can secure shell 610 relative connector body 630 to retain connector body 630 and plug 650 at least partially within shell 610.

Furthermore, and as embodied herein, valve 680 can include a port 682 to receive a fluid injecting device, for example and without limitation a syringe 430. For example and without limitation, the port 682 can be configured as an oral/enteral connector, luer connector, or any other suitable fluid-tight connector to receive a corresponding syringe. In this manner, fluid can be introduced through port 682 and exit port 689 into shell 610 and connector body 630 and through the G-tube 112 while bypassing the J-tube 114. This configuration can be utilized, for example, to flush the G-tube 112 with liquid or administer a liquid directly to the stomach through the G-tube 112.

With reference to FIGS. 17A-17C, and as embodied herein, a locking tool 690 can be used to secure valve 680 to shell 610. Locking tool 690 can have a hollow projection 696 defining a perimeter 693 and notches 691, each of which can correspond to one or more slots 684 defined within the top of valve 680. As such, projection 696 of locking tool 690 can be inserted into slots 684 to engage locking tool 690 to valve 680 such that turning locking tool 690 rotates valve 680 into engagement with shell 610. Locking tool can have a gripping portion 699 at a top thereof, and as embodied herein, can be wider than projection 696 and can be substantially flat. As embodied herein, locking tool 690 can be discarded after value 680 is secured to shell 610. Alternatively, locking tool 690 can be retained, for example to be utilized to cover port 682, when disposed within slots 684. and protect port 682 from debris.

According to another aspect, the disclosed subject matter includes a method of assembling a connector assembly for percutaneous tubing. The percutaneous tubing includes an outer tube, such as a G-tube, and an inner tube, such as a J-tube. The method includes providing a shell having a sidewall defining an interior, a first shell end having a first opening defined therein, a second shell end having a second opening defined therein, inserting the percutaneous tubing through the first and second openings of the shell, providing a connector body having a first body end and a second body end with a tube lumen defined therethrough, the first body end having a connector tip, inserting the inner J-tube into the connector tip and through the connector body, mating the outer G-tube with the connector tip, providing a plug having a first plug end and a second plug end with a fluid lumen defined therethrough, the first plug end having a plug tip extending therefrom, mating the inner J-tube with the plug tip, joining the connector body with the plug, and joining the connector body with the shell.

Any suitable fabrication technique can be used to form any of the tubing assembly and related components including, but not limited to, injection molding, milling or the like. The tubing assembly and related components can be formed of any suitable material including resilient polymers, for example but not limited to, thermoplastics, thermosets, elastomers and synthetic fibers or the like. For example and without limitation, and as embodied herein, connectors and components can include injection molded resins (e.g., methyl methacrylate, acrylonitrile butadiene/styrene (MABS)). Elastomeric seals or ferrules can include, for example and without limitation, silicon. O-rings can include, for example and without limitation, ethylene propylene diene monomer (EPDM), polyurethane, polytetrafluoroethylene, silicon, or any other suitable material, and can include a parylene coating. The plug tip and/or valve can include, for example and without limitation, stainless steel.

An exemplary technique for assembling a connector assembly 200 is illustrated in FIGS. 5-8. With reference to FIG. 5, a percutaneous tubing 110 having an outer G-tube 112 and an inner J-tube 114 is provided. The percutaneous tubing 110 has a free end 116 extending from a target location, for example and as embodied herein, a stoma. As shown for example in FIG. 5, the free end 116 of percutaneous tubing 110 can be inserted through the first shell end 214 opening and the second shell end 216 opening to extend the percutaneous tubing 110 through the interior of the shell 210.

Figure 6:
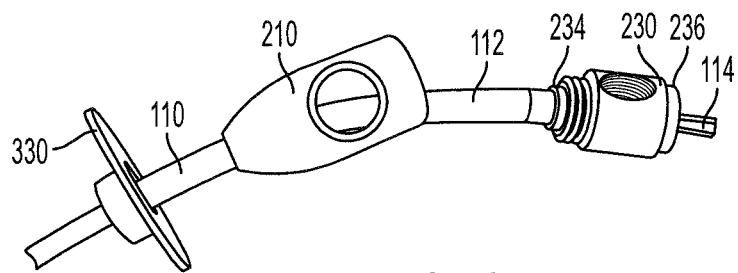
FIG. 6 is a perspective view of the percutaneous tubing of FIG. 5, with the J-tube inserted through an exemplary connector body and the G-tube mated with an exemplary connector tip according to the disclosed subject matter.

Referring now to FIG. 6, and with reference to the exploded view of FIGS. 4A-4C, the inner J-tube 114 is inserted into the connector tip 237 proximate first body end 234 and through the connector body 230, exiting the second body end 236. The outer G-tube 112 is mated with the connector tip 237, for example and as embodied herein, by inserting the connector tip 237 into the G-tube 112.

Figure 7:
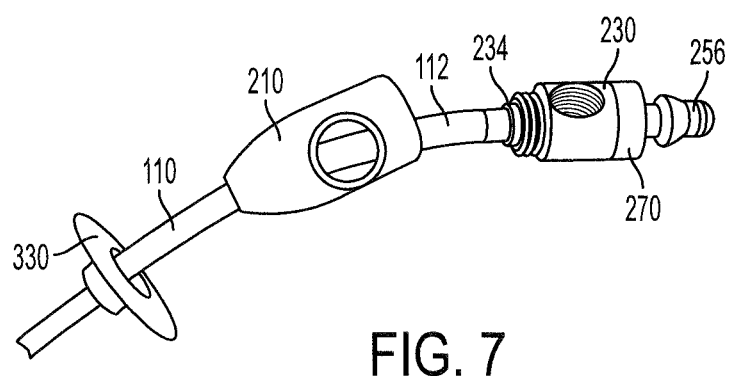
FIG. 7 is a perspective view of the percutaneous tubing of FIG. 6, with the J-tube mated with an exemplary plug tip and an exemplary plug joined to the connector body according to the disclosed subject matter.

With reference to FIG. 7, and continued reference to the exploded view of FIGS. 4A-4C, the plug tip 257 is inserted into the J-tube 114. The plug 250 can be urged toward the connector body 230 such that the connector body flange 244 and the plug flange 264 align with the protrusions 246 received within the recesses 266. The notches 275a, 275b of the clip 270 can be inserted into the groove 245 of the connector body 230 and the groove 265 of the plug 250 to join the plug 250 to the connector body 230. For example, as embodied herein, notches 275a, 275b of the first clip portion 272 can be inserted into each of the grooves 245, 265 and notches 275a, 275b of the second flip portion 274 can be inserted into each of the grooves 245, 265 to form a ring-shaped clip 270 about the flanges 244, 264 of the connector body 230 and plug 250.

Alternatively, with reference to the exploded view of the embodiment of FIGS. 17A-17C, locking projections 672 with locking ribs 675 of plug 650 can be urged into engagement with locking surfaces 674 to secure plug 650 to connector body 630 with flanges 646 of connector body disposed within recesses 666 of plug 650.

Figure 8:
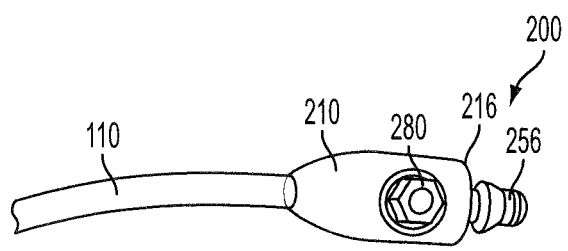
FIG. 8 is a perspective view of the percutaneous tubing of FIG. 7, with the connector body joined with the shell according to the disclosed subject matter.

Referring now to FIG. 8, and with reference to the exploded view of the embodiment of FIGS. 4A-4C, the connector body 230 with the plug 250 inserted therein can be urged into the interior of the shell 210 with the second plug end 256 extending from the second shell end 216. The connector body 230, plug 250 and J-tube 114 can be held in place, and the shell 210 can be joined to the connector body 230, for example and as embodied herein, by rotating shell 210 relative the connector body 230 such that the engagement portion 218 of the shell 210 engages the engaging portion 238 of the connector body 230. Shell 210 can be rotated relative connector body 230 such that aperture 220 aligns with aperture 240. Valve 280 can be inserted through aperture 220 into aperture 240 and engaging feature 282 can engage engagement feature 242 of the connector body 230, for example and as embodied herein, by rotating valve 280 into engagement with the connector body 230.

Alternatively, with reference to the embodiment of FIGS. 17A-17C, valve 680 can be inserted through aperture 620 into aperture 640 and locking finger 687 can engage engagement feature 617 of shell 610, for example and as embodied herein, by rotating valve 680 into engagement with shell 610, as described herein.

In the configuration of FIG. 8, the second end 256 of the plug 250 is in fluid communication with the J-tube 114, and can be joined with a device connector 400 for fluid communication with a device, such as a syringe 430 or pump 450 or other fluid source, as described further herein. Furthermore, as embodied herein, the valve 280 is in fluid communication with the G-tube, and can be joined via port 285 to a syringe 430 or pump 450 for fluid communication therewith.

With reference to FIG. 1, as embodied herein, a removable cap 290 can be provided, sized to cover the second plug end 256 of the connector assembly 200 and close the fluid lumen opening at the open plug nub 263 proximate the second plug end 256. The cap 290 can be a free cap, i.e., independent of the connector assembly 200. Alternatively, in some embodiments, the cap 290 can be tethered to the connector assembly 200, for example to the shell 210 or the plug 250.

Figure 13A:
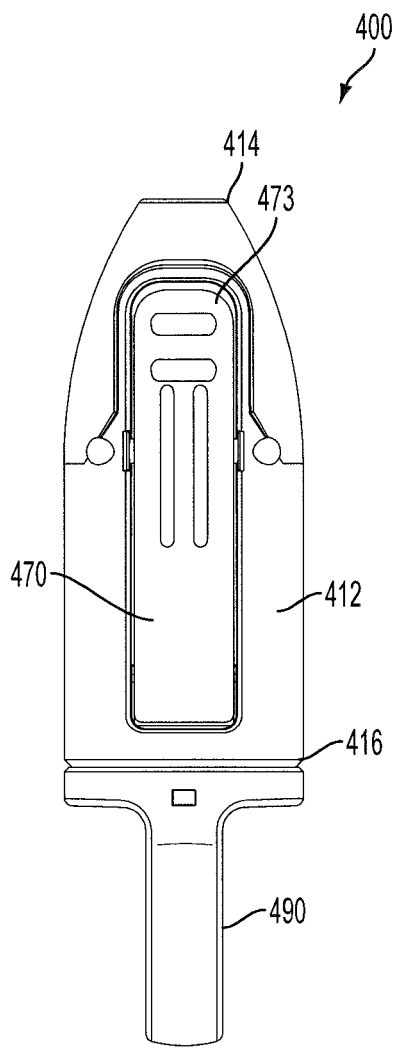
FIG. 13A is a top view of an exemplary female connector of the tubing system of FIG. 1, with a removable cap disposed thereon, according to an illustrative embodiment of the disclosed subject matter.
Figure 13B:
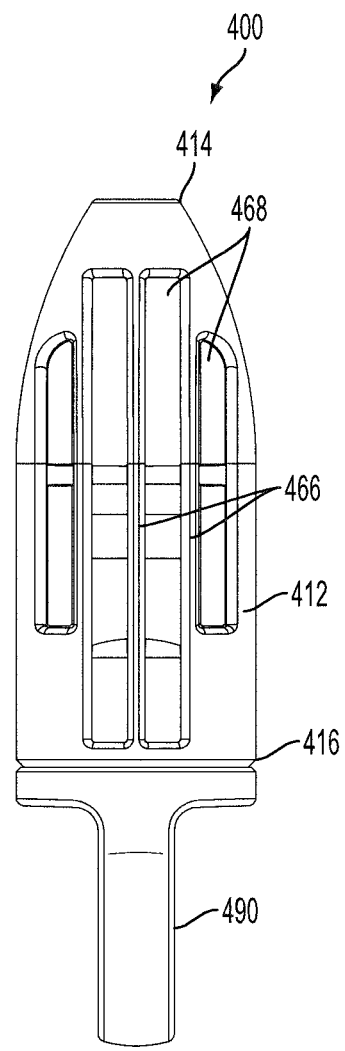
FIG. 13B is a bottom view of the female connector of FIG. 13A.
Figure 13E:
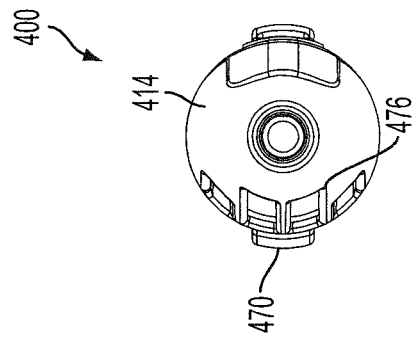
FIG. 13E is a front view of the female connector of FIG. 13A.
Figure 13D:
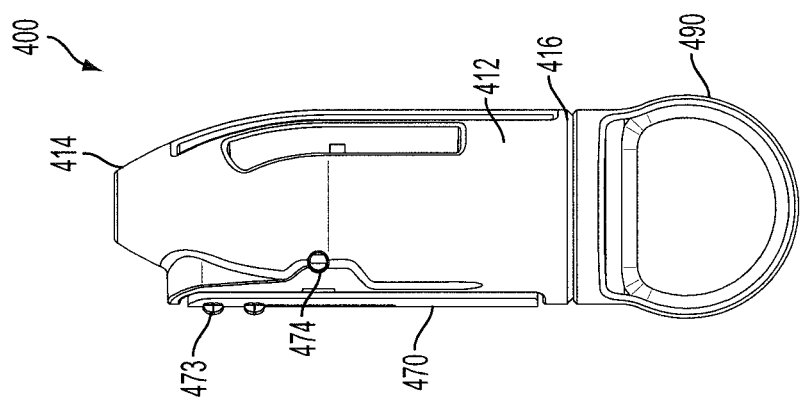
FIG. 13D is a right side view of the female connector of FIG. 13A.
Figure 13C:
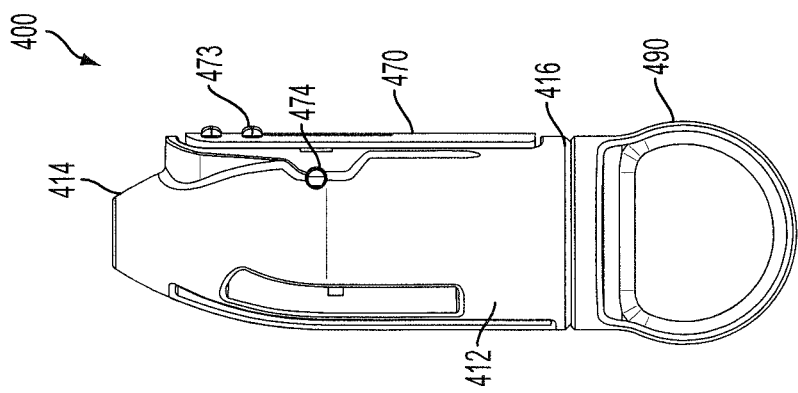
FIG. 13C is a left side view of the female connector of FIG. 13A.
Figure 14:
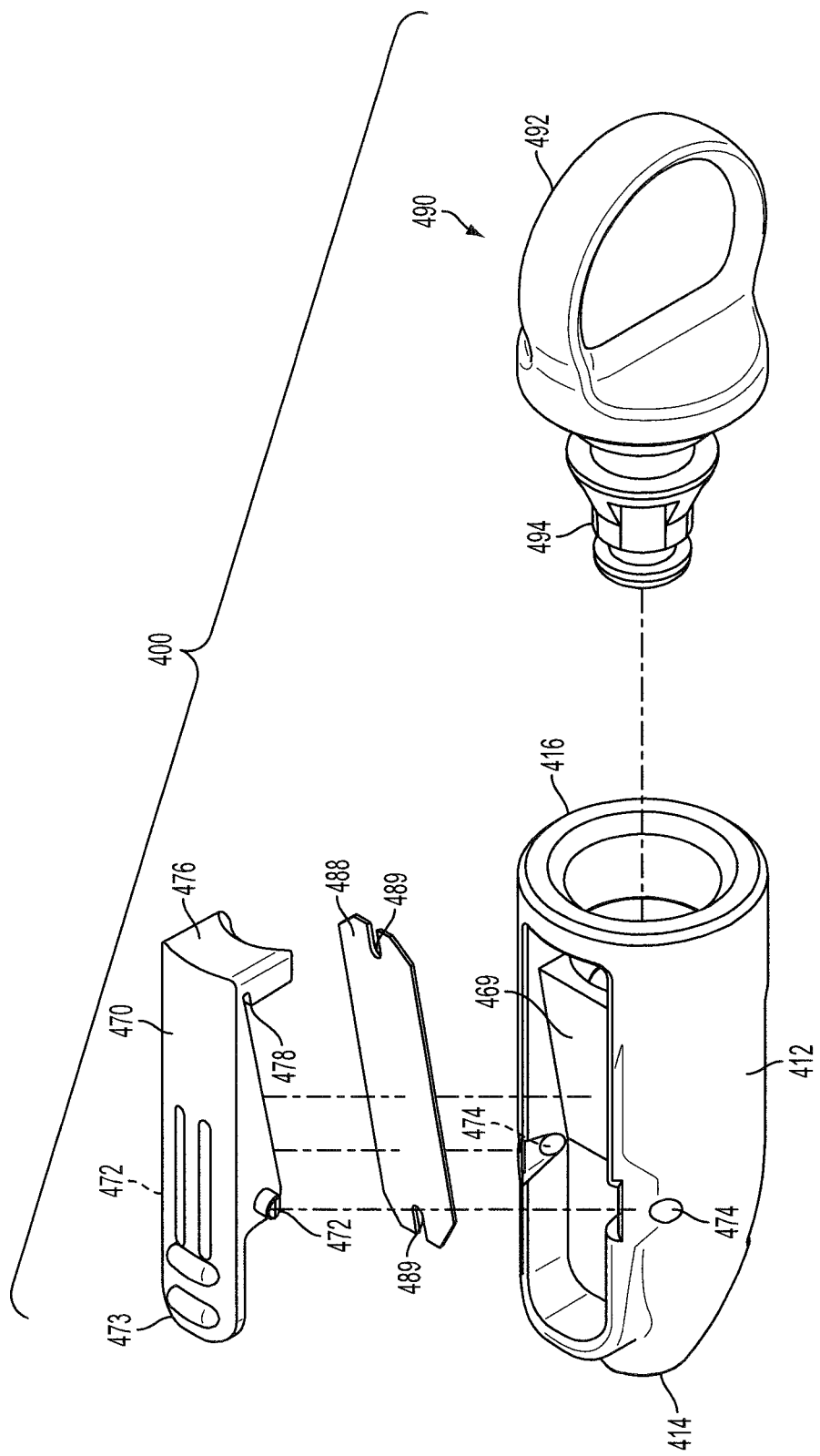
FIG. 14 is an exploded perspective view of the female connector of FIG. 13A.
Figure 15:
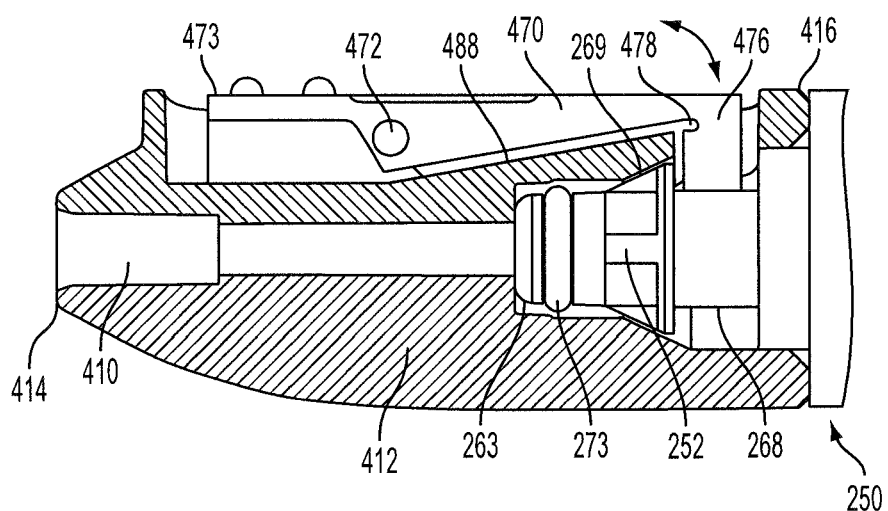
FIG. 15 is a cross-sectional view of the female connector of FIG. 13A in engagement with an exemplary second plug end.

Further in accordance with the disclosed subject matter, a device connector is provided to be coupled with the connector assembly disclosed herein. The device connector can be coupled a delivery device or fluid source. For purpose of illustration and not limitation, any number of suitable device connector configurations can be used to join percutaneous tubing 110 to any suitable fluid delivery device, for example and without limitation, as shown in FIG. 1, syringe 430 and/or pump 450. FIGS. 13A-14 illustrate an exemplary device connector 400. As embodied herein, device connector 400 can generally include a sidewall 412 having a first end 414 and a second end 416, a lever 470 and a plug 490.

The device connector 400 can include a sidewall 412 defining an interior of thereof and a first end 414 with an aperture therein sized to receive an end of tubing 410 extending from and in fluid communication with the delivery device (as shown for example in FIG. 1). The tubing 410 is likewise disposed in fluid communication with the interior of device connector 400. Device connector 400 can have a second end 416 with an aperture therein sized and configured to receive second plug end 256 of the connector assembly 200 or second plug end 656 of connector assembly 600 in sealing engagement. Additionally, and as embodied herein, sidewall 412 can include a number of ridges 466 defining a number of slots 468 in sidewall 412. Ridges 466 and slots 468 can provide a structure having improved moldability and can provide a textured surface for device connector 400 to improve the gripability thereof. The device connector 400 and/or the connector assembly 200 or 600 can be provided with a releasable connection feature to join the device connector 400 to the connector assembly 200. A variety of quick connectors can be used, such as a lever 470, as embodied herein. Lever 470 can be hingedly joined to sidewall 412 by lever projections 472 received in apertures 474 in sidewall 412. Lever 470 can also include a locking extension 476 to engage a mating portion of connector assembly 200 or 600, such as second plug end 256 or 656, respectively, as described herein. Lever 470 can thus provide a releasable engagement for device connector 400 to connector assembly 200 or 600.

As shown for example in FIG. 14, device connector 400 can further include a biasing plate 488 disposed along ramped surface 469 in the interior of device connector 400. Biasing plate 488 can be disposed within slot 478 of lever 470 to bias locking extension 476 into a locking position. Biasing plate 488 can include one or more notches 489 on one or more ends thereof, which can be sized and configured to receive a corresponding projection on lever 470, for example to align biasing plate 488 with locking extension 476 and/or free end 473. For example, and as embodied herein, as shown in FIG. 13E, in the locking position, locking extension 476 can be biased into alignment with the second end 416 aperture of device connector 400. In this configuration, when second plug end 256 of connector assembly 200 is inserted into the second end 416 aperture of device connector 400, locking extension 476 of the lever can cam along frustoconical portion 269 of the second plug end 256 and insert into groove 268 of the second plug end, as shown for example in FIG. 15. In this manner, as embodied herein, locking extension 476 can join device connector 400 axially with connector assembly 200 with percutaneous tubing 110 for fluid communication with the interior of device connector 400 and tubing 410. Additionally, as embodied herein, locking extension 476 can be free to slide along the circumference of groove 268, and thus device connector 400 can rotate relative connector assembly 200 while remaining in axial engagement.

As such, as embodied herein, connector assembly 200 can provide a secure sealed connection between percutaneous tubing 110 and device connector 400, inhibiting or preventing an accidental disconnect and dislocation of the percutaneous tubing 110. Moreover, the connection does not require a twist connection. Rather, for example and as embodied herein, a linear push fit can be utilized. Once connected, the delivery device is joined to the connector assembly 200, and thus the percutaneous tubing 110, for delivery of a therapeutic agent to the patient.

With reference to FIG. 14, lever 470 can have a free end 473 opposite locking extension 476. To disconnect device connector 400 from connector assembly 200, pressure can be applied to urge free end 473 at least partially within sidewall 412 to overcome the bias force of biasing plate 488 and move locking extension 476 out of alignment with second end 416 aperture of device connector 400, and thus out of groove 268 of second plug end 256. In this configuration, connector assembly 200 is free to be removed from device connector 400.

Additionally, with reference to FIG. 14, cover 490 of device connector 400 can be used to cover the second end 416 aperture when connector assembly 200 is not connected. Cover 490 can include a grip portion 492 to facilitate gripping of cover 490. Cover 490 can include a cover end 494, which can be configured substantially similar to second plug end 256 of connector assembly 200, as described herein.

According to another aspect, the disclosed subject matter includes a bumper for a tubing assembly including percutaneous tubing. The bumper is configured to prevent or inhibit axial movement of the percutaneous tubing. The bumper includes a base having an aperture defined therethrough sized to receive the percutaneous tubing, a first bumper base portion and a second bumper base portion, each of the first bumper base portion and the second bumper base portion having a notch defining a portion of the aperture, and a connector to connect the first and second bumper base portions together. The bumper can include any or all of the features as described herein.

Figure 9A:
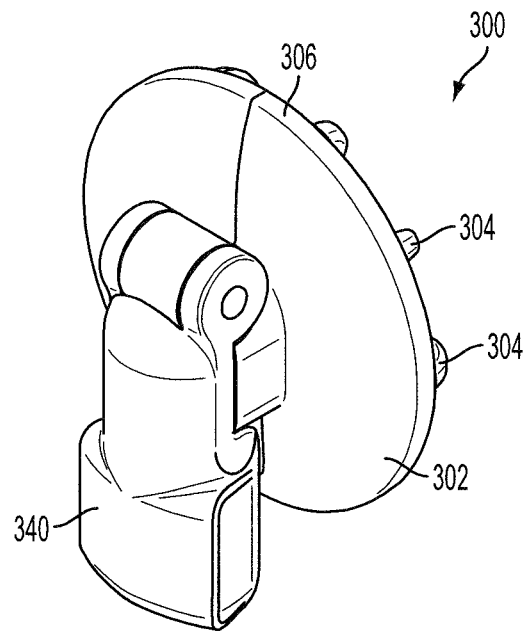
FIG. 9A is a perspective view of an exemplary bumper of the exemplary tubing system of FIG. 1.
Figure 9B:
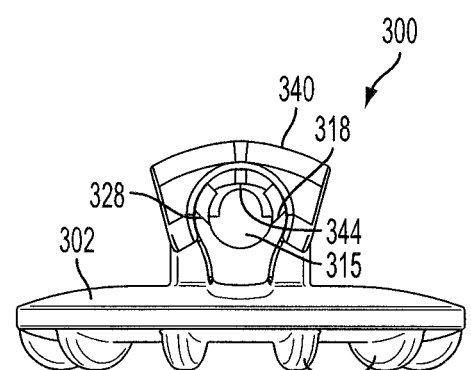
FIG. 9B is a front view of the exemplary bumper of FIG. 9A.
Figure 9C:
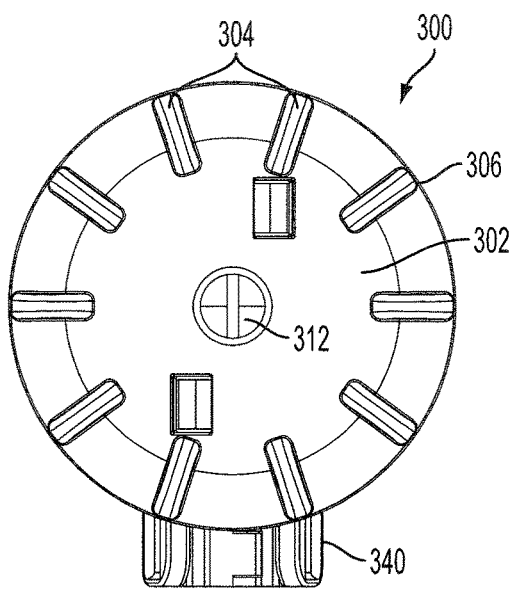
FIG. 9C is a bottom view of the exemplary bumper of FIG. 9A.
Figure 10:
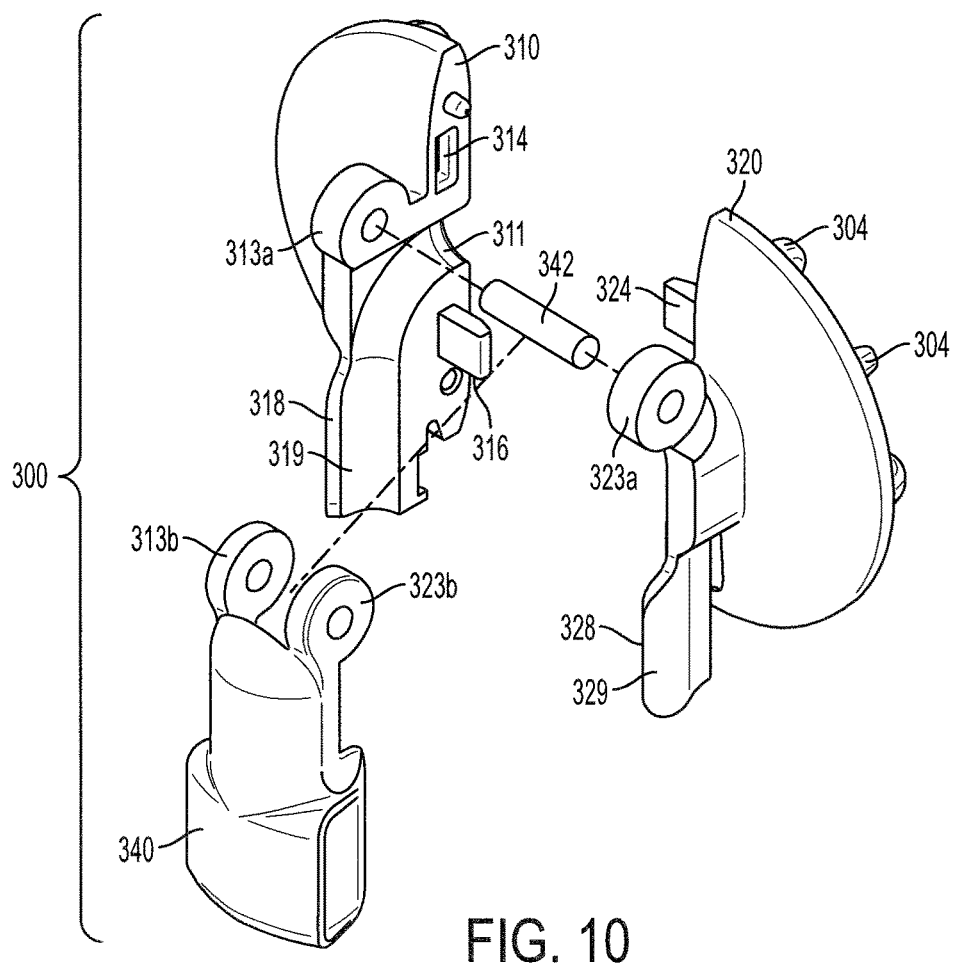
FIG. 10 is an exploded perspective view of the exemplary bumper of FIG. 9A.

An exemplary bumper 300 for a tubing system 100 is illustrated in FIGS. 9A-10. As discussed further herein, bumper 300 can be configured to be disposed about the percutaneous tubing 110 to inhibit or prevent axial movement of the percutaneous tubing 110. With reference to FIGS. 9A-9C, bumper 300 can include a base 302 having an aperture 312 defined therethrough. A plurality of protuberances 304 can be formed on a bottom surface of base 302. Base 302 can be generally flat and can include an arcuate perimeter 306, or other suitable shape.

In certain embodiments, base 302 can be a single piece member, such that the percutaneous tubing 110 is threaded through the aperture. Alternatively, a multi-piece configuration can be provided. With reference to FIG. 10, as embodied herein, bumper 300 can include a first bumper base portion 310 and a second bumper base portion 320. As shown for example in FIG. 10, first bumper base portion 310 generally can minor second bumper base portion 320. Each of the first bumper base portion and the second bumper base portion can have a notch 311 defining a portion of the aperture. The first and second bumper base portions 310, 320 can be connected together, for example and as embodied herein, with a projection 324 extending from one of the bumper base portions 310, 320 inserted into a receptacle 314 defined within the other bumper base portion 310, 320. Additionally or alternatively, first bumper base portion 310 can include a projection 316 to be inserted into a receptacle defined within the second bumper base portion 320.

Furthermore, and as embodied herein, the first and second bumper base portions 310, 320 can each include a support wall 318, 328 located proximate the notch 311 of each of the first and second bumper base portions 310, 320. With reference to FIG. 10, a hood 340 can be hingedly connected to the support wall 318, 328 of each of the first and second bumper base portions 310, 320, for example and as embodied herein, by a pin 342 inserted through ring projections 313a, 323a extending from each support wall 318, 328 and corresponding ring projections 313b, 323b extending from the hood 340.

With reference to FIGS. 9A-10, as embodied herein, each support wall 318, 328 can have a curved wall surface 319, 329 to define a portion of a U-shaped channel 315 extending from the aperture 312 and sized to receive the percutaneous tubing 110 when the first and second bumper base portions 310, 320 are connected together. Channel 315 can be aligned at a substantially perpendicular orientation relative to the flat surface proximate the aperture 312 and then curve so as to be aligned at an angle relative to the substantially perpendicular orientation. For example, channel 315 can extend along each support wall 318, 328 so as to be aligned substantially parallel to the flat surface 302 at a distance from the aperture 312. In this manner, channel 315 can maintain percutaneous tubing 110 therein from an orientation substantially perpendicular to the stoma, which can reduce contact with skin surrounding the stoma and promote stoma healing, and then guide the percutaneous tubing 110 to an alternate angle at a distance from the aperture 312, such as for a lower profile. Furthermore, as embodied herein, the patient can change radial orientation of the percutaneous tubing 110 relative the aperture 312 without changing the orientation of the percutaneous tubing 110 relative the stoma. In this manner, and as embodied herein, bumper 300 allows patients to direct percutaneous tubing 110 in any radial direction from the aperture 312, such as within the parallel plane of the patient's abdomen. As embodied herein, bumper 300 thus can maintain the portion of the percutaneous tubing 110 exiting bumper 300 in a substantially flat profile, which can be less noticeable and more comfortable to the patient. With the bumper 300 disclosed herein, the percutaneous tubing 110 can be oriented in any radial direction, for example to accommodate clothing or accessories worn or used by the patient.

Figure 11:
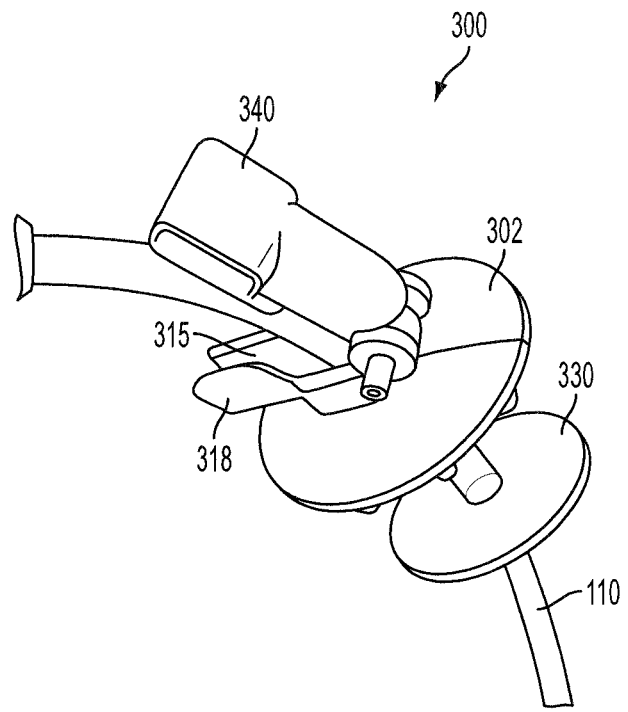
FIG. 11 is a perspective view of the exemplary bumper of FIG. 9A, with percutaneous tubing inserted therethrough and a hood in an open position.
Figure 12:
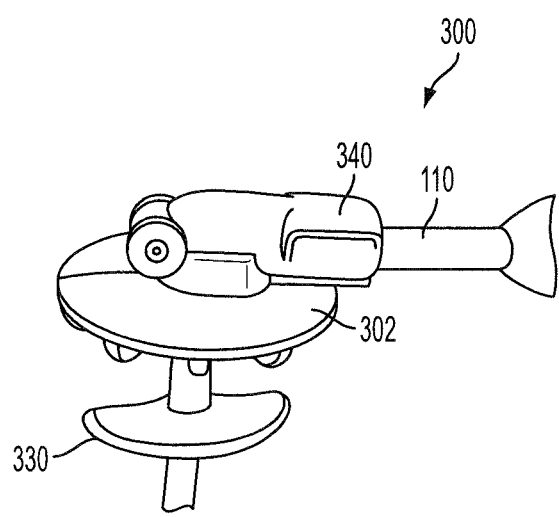
FIG. 12 is a perspective view of the exemplary bumper of FIG. 9A, with the hood in a closed position.

Furthermore, and as embodied herein, hood 340 can have a U-shaped surface 344 sized to receive a portion of the percutaneous tubing 110. Referring now to FIGS. 11-12, as embodied herein, with the percutaneous tubing extending along the channel 315, the hood 340 can be moveable between an open position, as shown in FIG. 11, with the bumper freely moveable relative to the percutaneous tubing, and a closed position, as shown in FIG. 12, with the bumper 300 secured relative to the percutaneous tubing 110. In the closed position, the U-shaped surface 344 of the hood 340 can overlap at least a portion of the support walls 318, 328 such that the hood 340 can enclose a portion of the percutaneous tubing 110 within the channel 315 and thus guide the percutaneous tubing 110 extending from the aperture 312 to the desired angle, e.g., a position proximate to and substantially parallel with the flat surface of base 302.

Any suitable fabrication technique can be used to form any of the tubing assembly and related components including, but not limited to, injection molding, milling or the like.

The tubing assembly and related components can be formed of any suitable material including resilient polymers, for example but not limited to, thermoplastics, thermosets, elastomers and synthetic fibers or the like. The bumper can include, for example and without limitation, injection molded resin (e.g., MABS) and can include a thermoplastic elastomer (TPE) overmold.

Additionally, and as embodied herein, the bumper 300 can include a cushion 330 disposed along the percutaneous tubing 110 inside the body of the patient, and thus disposed on an opposing side of the stoma from the bumper 300. As such, cushion 330 can provide a flexible anchor to retain a portion of the percutaneous tubing 110 within the body. Cushion 330 can be made of a soft and flexible material compared to the bumper 300, for example a polymeric material, and can have a silicon overmold.

Figure 18A:
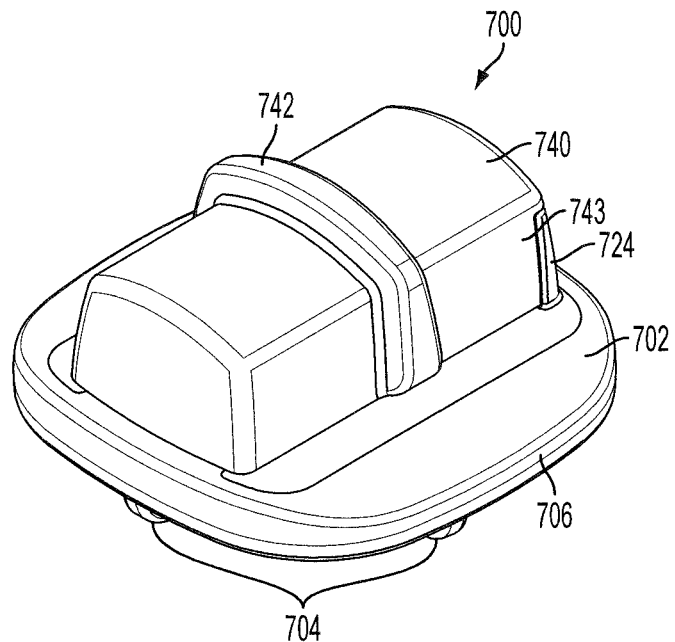
FIG. 18A is a perspective view of another embodiment of an exemplary bumper of the exemplary tubing system of FIG. 1.
Figure 18B:
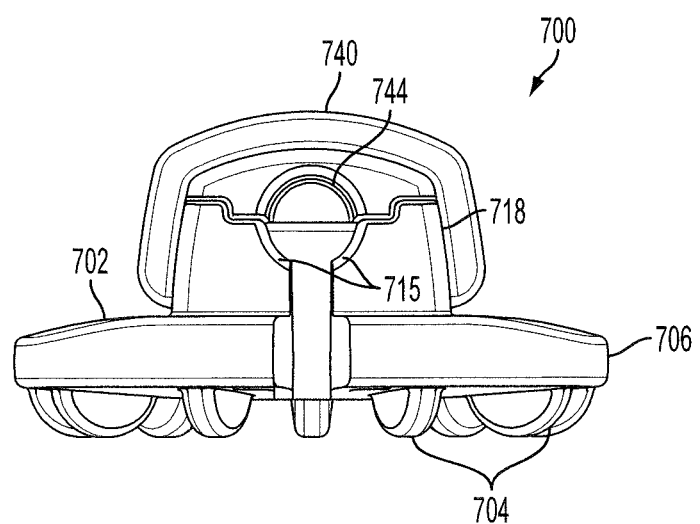
FIG. 18B is a front view of the exemplary bumper of FIG. 18A.
Figure 18C:
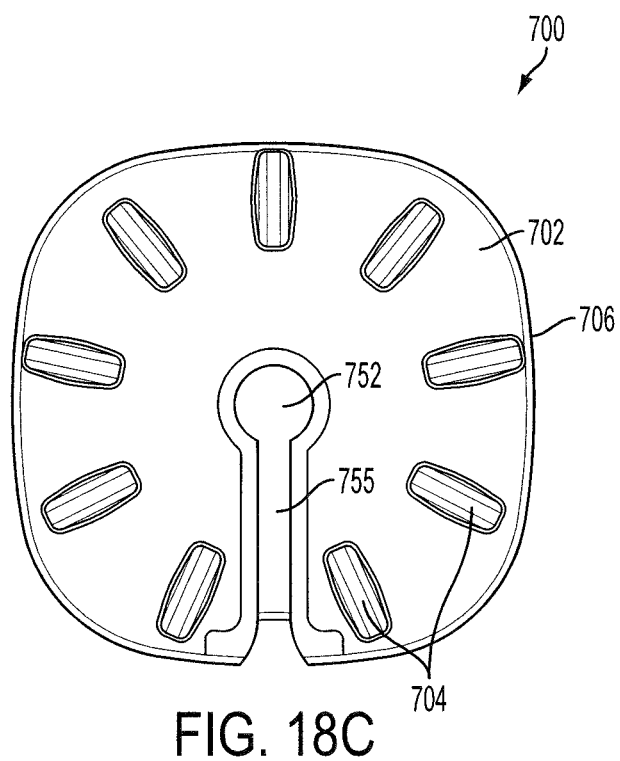
FIG. 18C is a bottom view of the exemplary bumper of FIG. 18A.

With reference to FIGS. 18A-19B, an alternative embodiment of an exemplary bumper 700 is illustrated. As discussed herein, bumper 700 can be configured to be disposed about the percutaneous tubing 110 to inhibit or prevent axial movement of the percutaneous tubing 110. With reference to FIG. 18A-18C, bumper 700 can include a base 702 having an aperture 712 defined therethrough. A plurality of protuberances 704 can be formed on a bottom surface of base 702. Base 702 can be generally flat and can include an arcuate perimeter 706, or other suitable shape. Protuberances 704 can provide a gap between base 702 and the stoma, which can improve airflow to the stoma, thereby improving healing and/or reducing or preventing infection of the skin around the stoma. As embodied herein, protuberances 704 can have an outer surface with a rounded or arcuate shape, which can improve comfort when bumper 700 engages the skin around the stoma. Additionally, protuberances 704 can provide a surface having increased traction to prevent or inhibit unwanted movement of bumper 700 relative the stoma, for example when hood 740 is being opened or closed, as described herein.

Figure 19A:
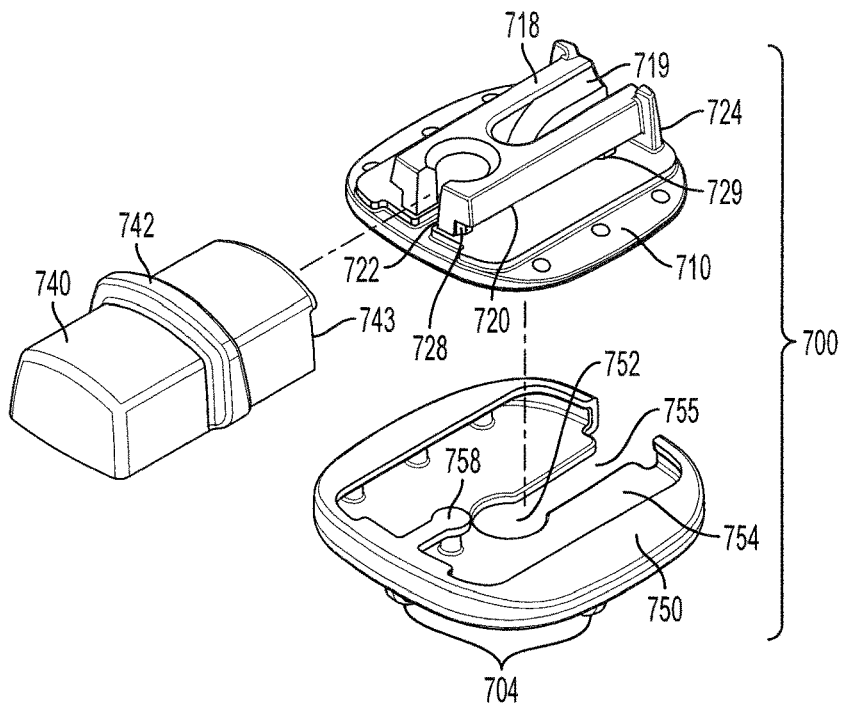
FIG. 19A is an exploded top perspective view of the exemplary bumper of FIG. 18A.
Figure 19B:
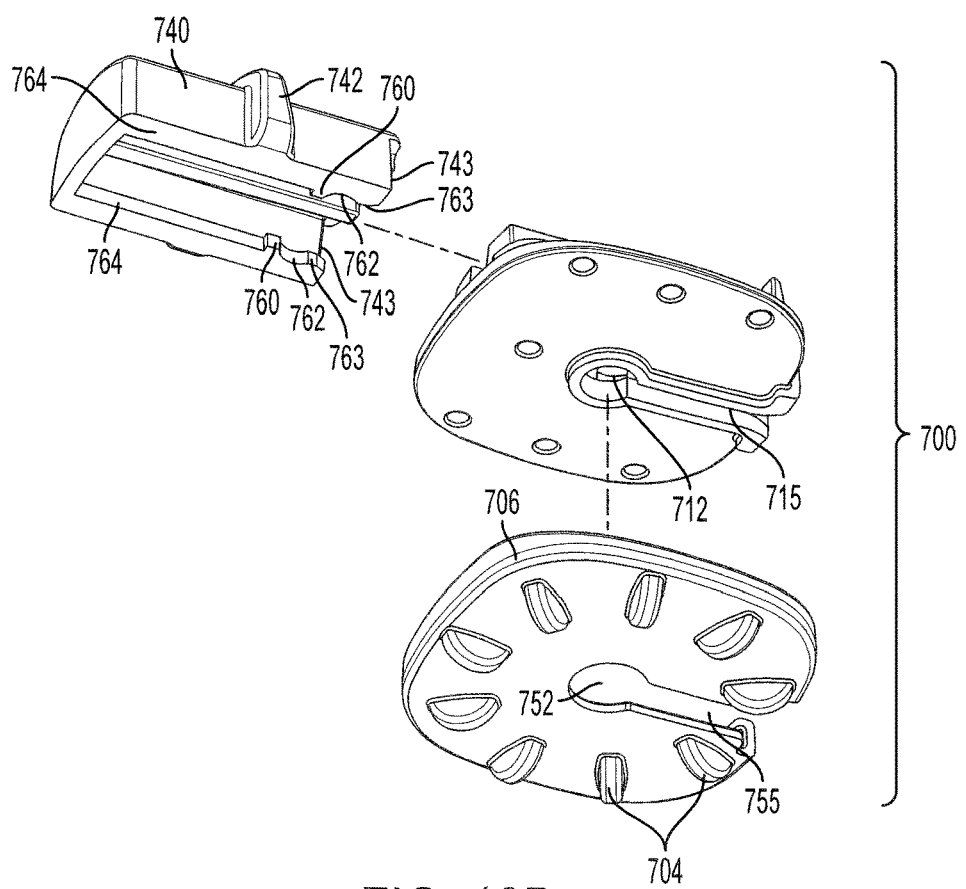
FIG. 19B is an exploded bottom perspective view of the exemplary bumper of FIG. 18A.

In certain embodiments, the base can be a single piece member, such that the percutaneous tubing 110 is threaded through the aperture. Alternatively, a multi-piece configuration can be provided. With reference to FIGS. 19A-19B, as embodied herein, base 702 can include a base portion 710 and a substrate portion 750 to house the base portion 710. As shown for example in FIG. 19A-19B, substrate portion 750 can have a recess 754 defined therein and sized to receive base portion 710. Substrate portion 750 can have an aperture 752 and channel 755 positioned in alignment with aperture 712 and channel 715, respectively, of base portion 710 received within substrate portion 750. Additionally, as embodied herein, substrate portion 750 can include a key projection 758 sized to be received within a corresponding slot 722 of base portion 710 to secure base portion 710 within substrate portion 750.

Furthermore, and as embodied herein, base portion 710 can include a support wall 718 located proximate aperture 712. With reference to FIGS. 19A-19B, a hood 740 can be slidably joined to base 702 within tracks 720, which can be defined by support wall 718. For example and as embodied herein, rails 764 on opposing sides of hood 740 can be inserted into and slide within tracks 720, which can be defined on opposing sides of support wall 718. Support wall 718 can include one or more lateral projections 724 which can engage one or more engagement portions 743 of hood 740 to limit lateral movement of hood 740 into a closed position, as discussed herein. In addition, and as embodied herein, track projections 729 disposed along each of tracks 720 proximate lateral projections 724 can be sized to be received within rail recesses 762, defined between projections 760 and 763 along each of rails 764, to secure hood 740 in the closed position. Hood 740 can be moved toward the open position, for example by urging hood 740 away from lateral projections 724 to urge track projections 729 out of engagement with recesses 762 of rails 764. Projections 760 can abut corresponding track projection 728 to limit lateral movement of the hood 740 in the direction toward the open position to retain rails 764 disposed within tracks 720. In this manner, hood 740 can be configured to be retained in engagement with base member 710, for example to prevent or inhibit inadvertent removal of hood 740 from base member 710.

With reference to FIGS. 18A-19B, as embodied herein, opposing sides of support wall 718 each can have a contoured recess 719 defining a portion of U-shaped channel 715 extending from the aperture 712 and sized to receive the percutaneous tubing 110. Contoured recess 719 can be aligned at a substantially perpendicular orientation relative to the flat surface proximate the aperture 712 and then curve so as to be aligned at an angle relative to the substantially perpendicular orientation. For example, contoured recess 719 can extend along support wall 718 so as to be aligned substantially parallel to the flat surface 702 at a distance from the aperture 712. In this manner, contoured recess 719 can maintain percutaneous tubing 110 therein from an orientation substantially perpendicular to the stoma, which can reduce contact with skin surrounding the stoma and promote stoma healing, and then guide the percutaneous tubing 110 to an alternate angle at a distance from the aperture 712, such as for a lower profile. Furthermore, as embodied herein, the patient can change radial orientation of the percutaneous tubing 110 relative the aperture 712 without changing the orientation of the percutaneous tubing 110 relative the stoma. In this manner, and as embodied herein, bumper 700 allows patients to direct percutaneous tubing 110 in any radial direction from the aperture 712, such as within the parallel plane of the patient's abdomen. As embodied herein, bumper 300 thus can maintain the portion of the percutaneous tubing 110 exiting bumper 700 in a substantially flat profile, which can be less noticeable and more comfortable to the patient. With the bumper 700 disclosed herein, the percutaneous tubing 110 can be oriented in any radial direction, for example to accommodate clothing or accessories worn or used by the patient.

Figure 20:
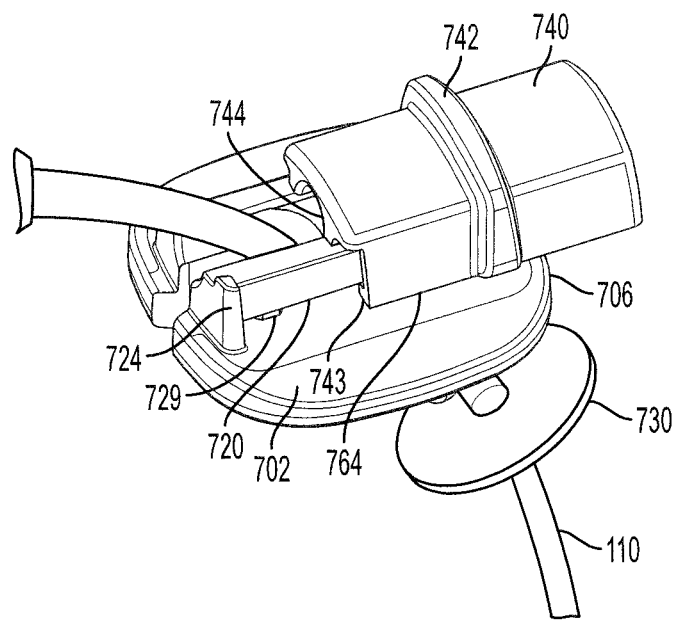
FIG. 20 is a perspective view of the exemplary bumper of FIG. 18A, with percutaneous tubing inserted therethrough and a hood in a first position.
Figure 21:
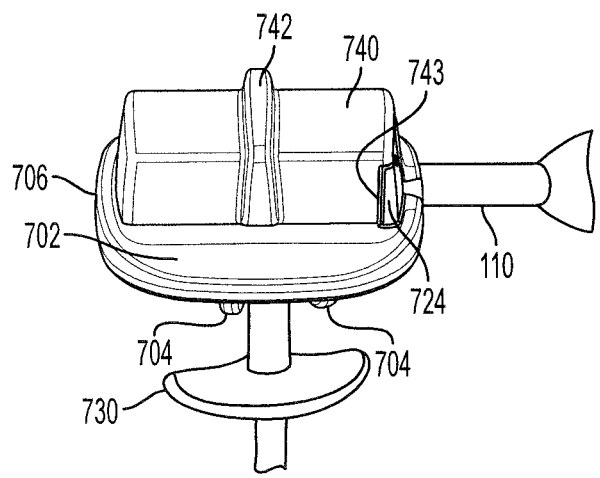
FIG. 21 is a perspective view of the exemplary bumper of FIG. 18A, with the hood in a second position.
Figure 22E:
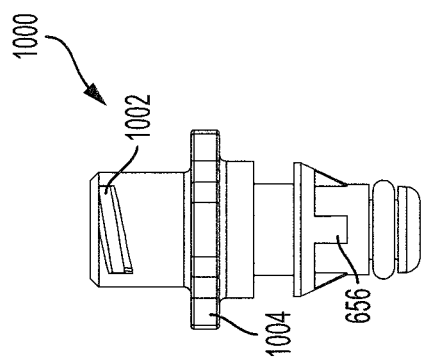
FIG. 22E is a top view of the exemplary male adapter of FIG. 22A, the bottom view being a mirror image of the top view.
Figure 22F:
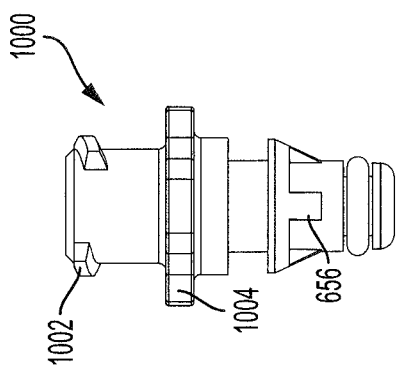
FIG. 22F is a left side view of the exemplary male adapter of FIG. 22A, rotated 90 degrees with respect to FIG. 22E, the right side view being a mirror image of the left side view.
Figure 22C:
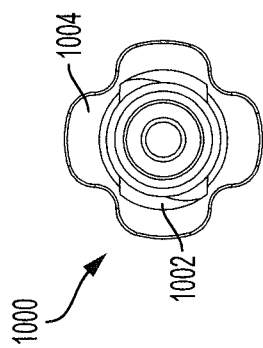
FIG. 22C is a rear view of the exemplary male adapter of FIG. 22A.
Figure 22D:
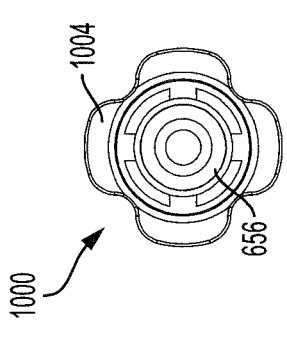
FIG. 22D is a front view of the exemplary male adapter of FIG. 22A.
Figure 22B:
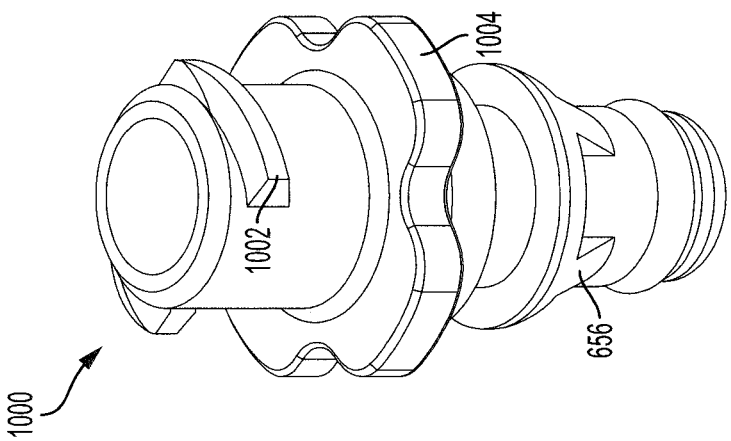
FIG. 22B is a rear perspective view of the exemplary male adapter of FIG. 22A.
Figure 22A:
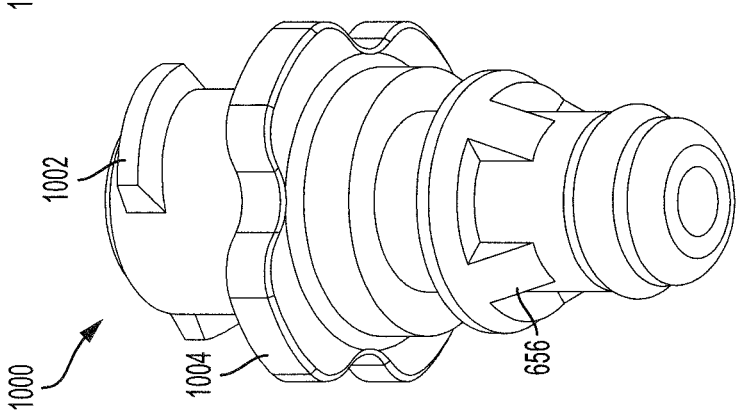
FIG. 22A is a front perspective view of an exemplary male adapter to the exemplary male connector assembly of FIG. 16A according to an illustrative embodiment of the disclosed subject matter.
Figure 23E:
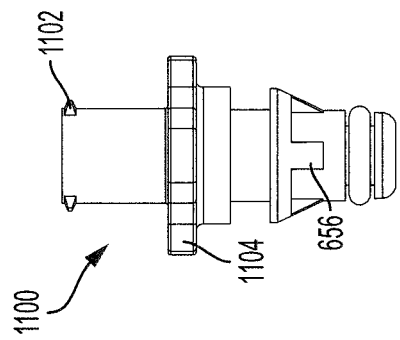
FIG. 23E is a top view of the exemplary male adapter of FIG. 23A, the bottom view being a mirror image of the top view.
Figure 23F:
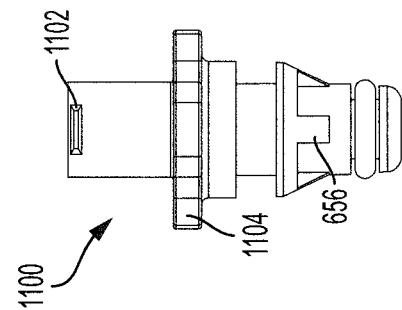
FIG. 23F is a left side view of the exemplary male adapter of FIG. 23A, the right side view being a mirror image of the left side view.
Figure 23C:
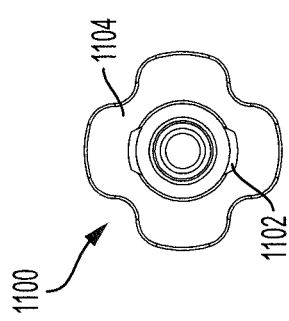
FIG. 23C is a rear view of the exemplary male adapter of FIG. 23A.
Figure 23D:
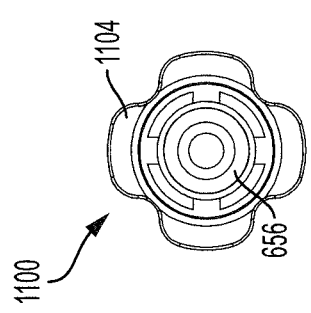
FIG. 23D is a front view of the exemplary male adapter of FIG. 23A.
Figure 23B:
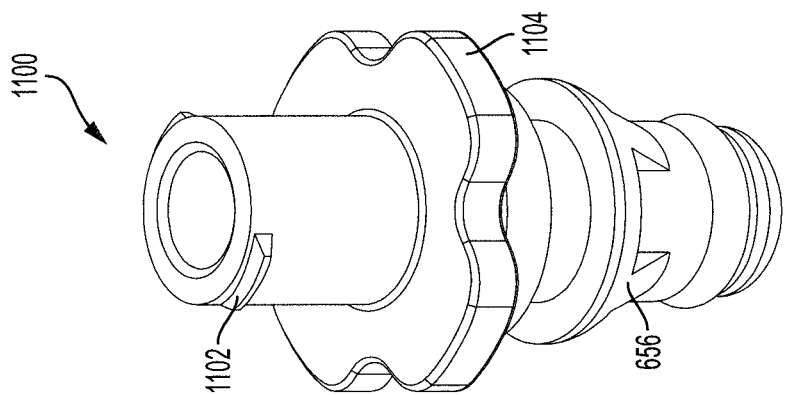
FIG. 23B is a rear perspective view of the exemplary male adapter of FIG. 23A.
Figure 23A:
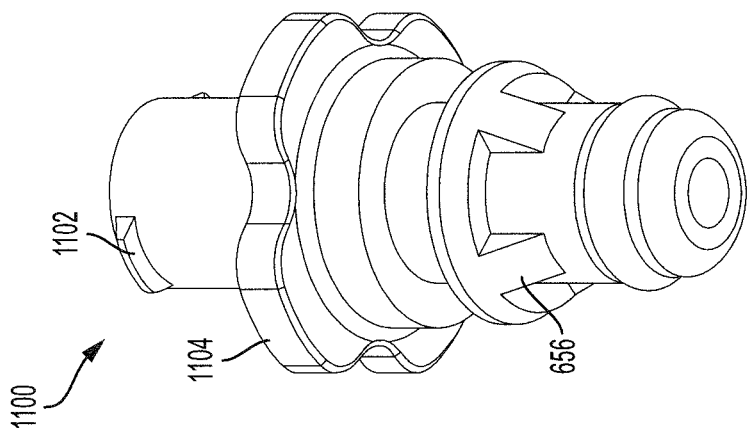
FIG. 23A is a front perspective view of another exemplary male adapter to the exemplary male connector assembly of FIG. 16A according to an illustrative embodiment of the disclosed subject matter.
Figure 24A:
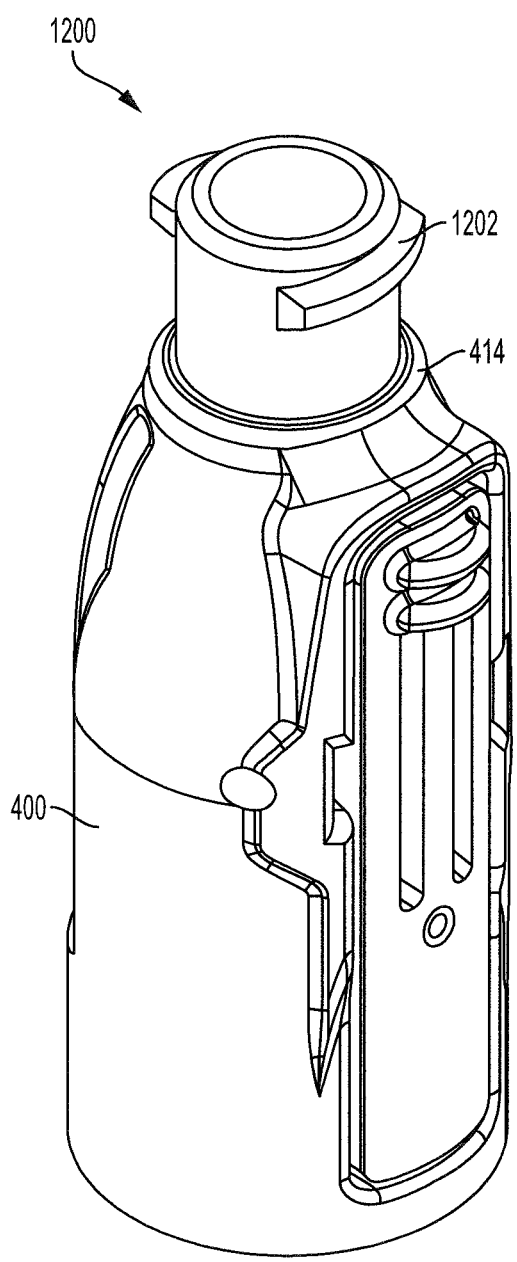
FIG. 24A is a front perspective view of an exemplary female adapter to the exemplary female connector assembly of FIG. 13A according to an illustrative embodiment of the disclosed subject matter.
Figure 24B:
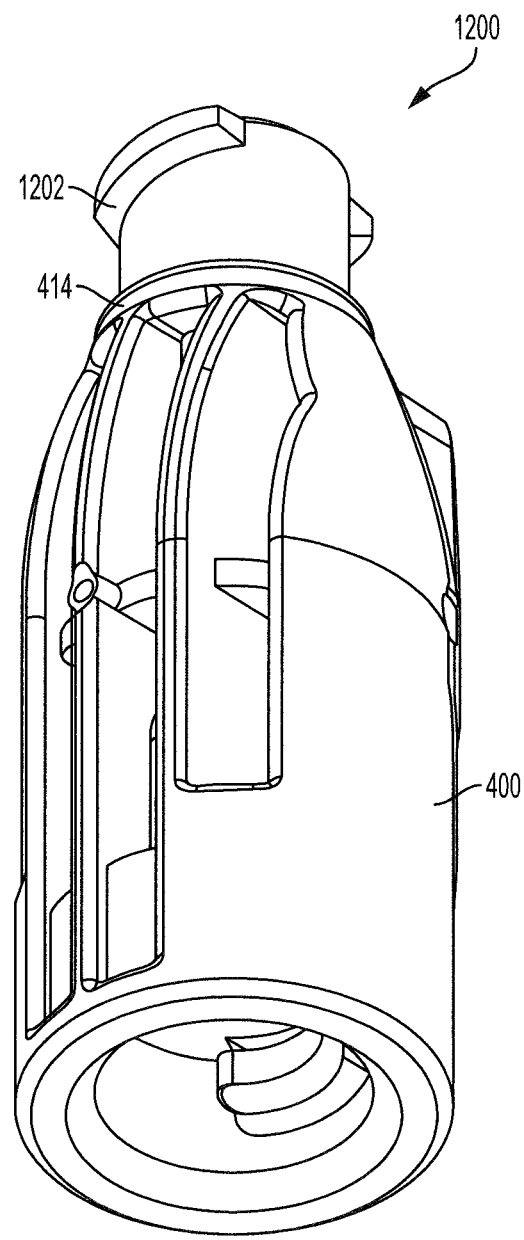
FIG. 24B is a rear perspective view of the exemplary female adapter of FIG. 24A.
Figure 24C:
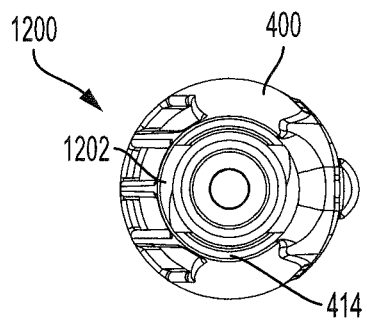
FIG. 24C is a rear view of the exemplary female adapter of FIG. 24A.
Figure 24F:
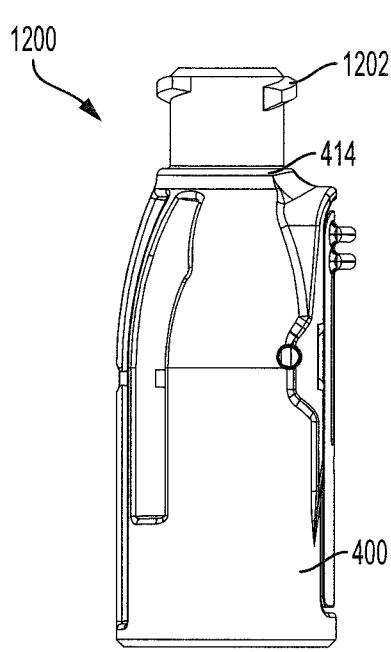
FIG. 24F is a left side view of the exemplary female adapter of FIG. 24A, the right side view being a mirror image of the left side view.
Figure 24D:
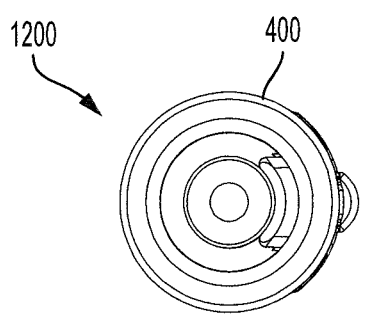
FIG. 24D is a front view of the exemplary female adapter of FIG. 24A.
Figure 24H:
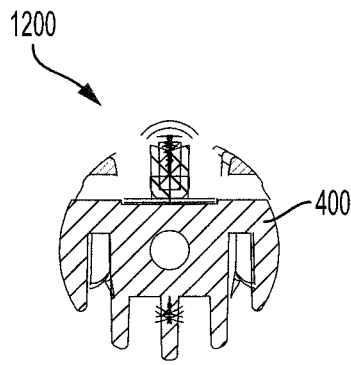
FIG. 24H is a cross-sectional view of the exemplary female adapter taken along line H-H of FIG. 24G.
Figure 24E:
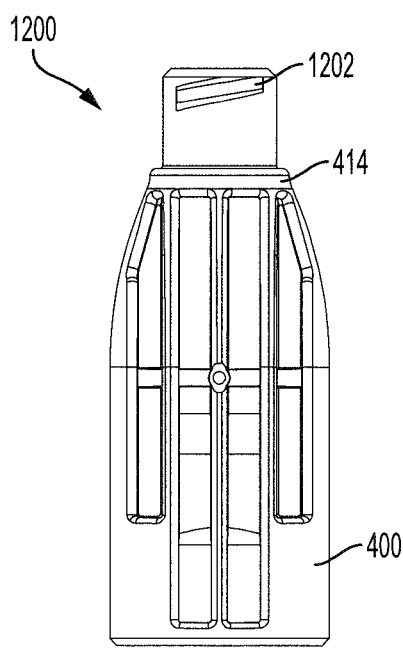
FIG. 24E is a bottom view of the exemplary female adapter of FIG. 24A.
Figure 24G:
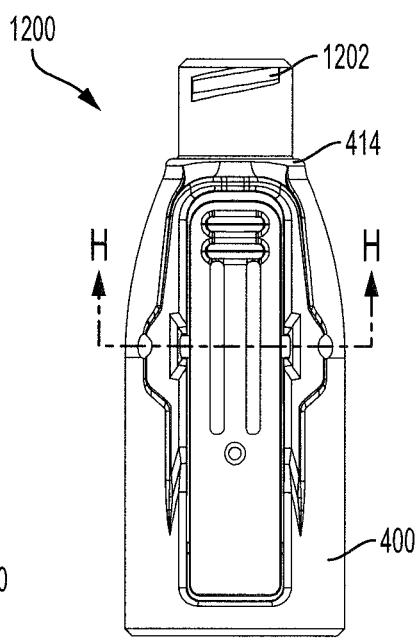
FIG. 24G is a top view of the exemplary female adapter of FIG. 24A.
Figure 25A:
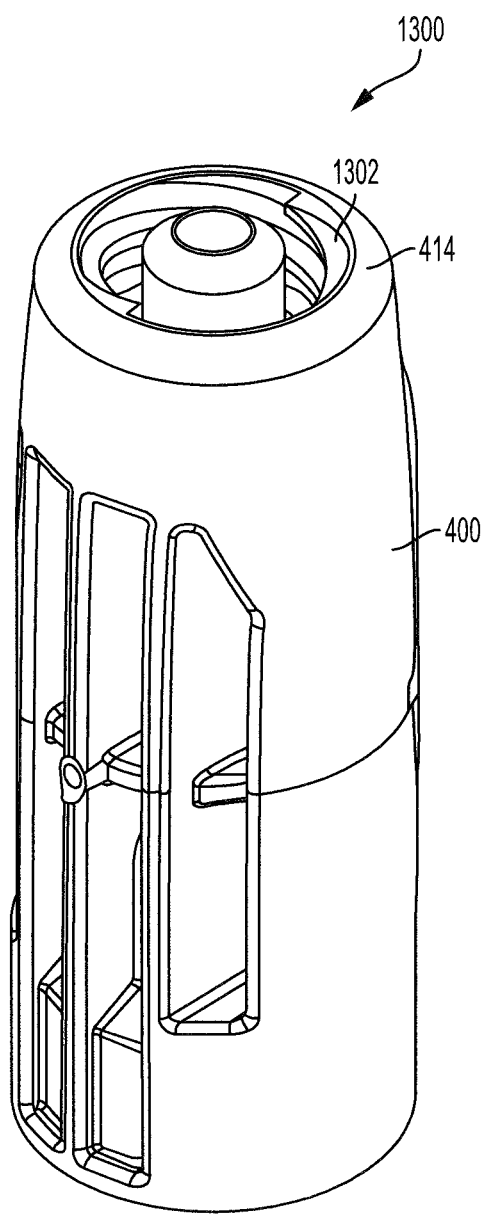
FIG. 25A is a rear perspective view of an exemplary male adapter to the exemplary female connector assembly of FIG. 13A according to an illustrative embodiment of the disclosed subject matter.
Figure 25B:
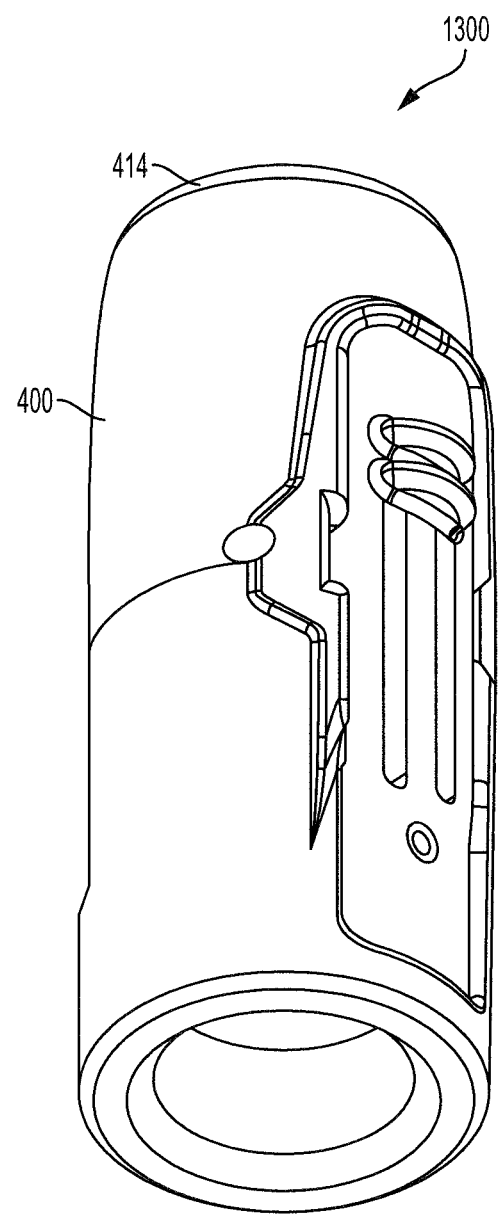
FIG. 25B is a front perspective view of the exemplary female adapter of FIG. 25A.
Figure 25C:
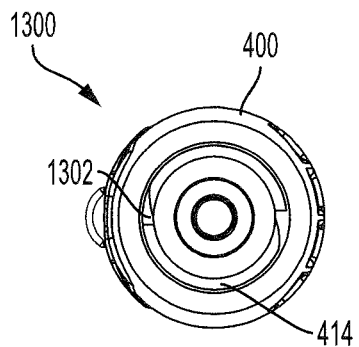
FIG. 25C is a rear view of the exemplary female adapter of FIG. 25A.
Figure 25E:
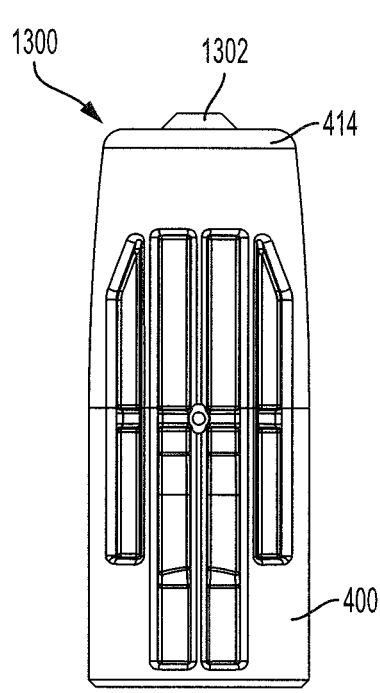
FIG. 25E is a bottom view of the exemplary female adapter of FIG. 25A.
Figure 25F:
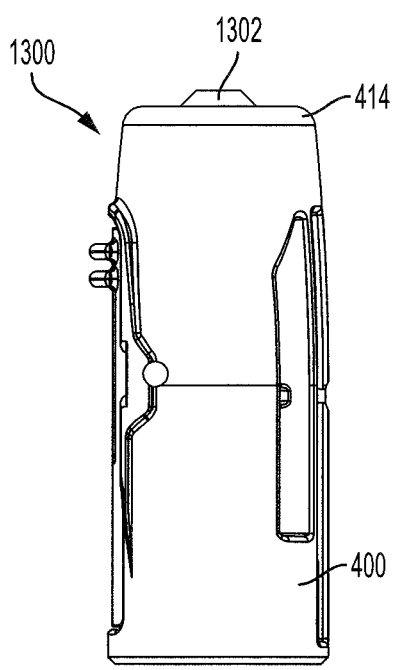
FIG. 25F is a right side view of the exemplary female adapter of FIG. 25A, the left side view being a mirror image of the right side view.
Figure 25D:
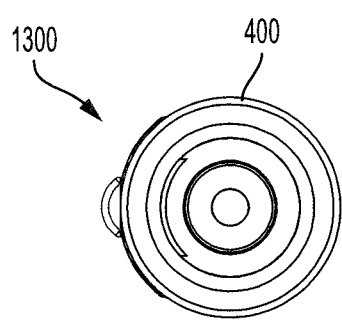
FIG. 25D is a front view of the exemplary female adapter of FIG. 25A.
Figure 25G:
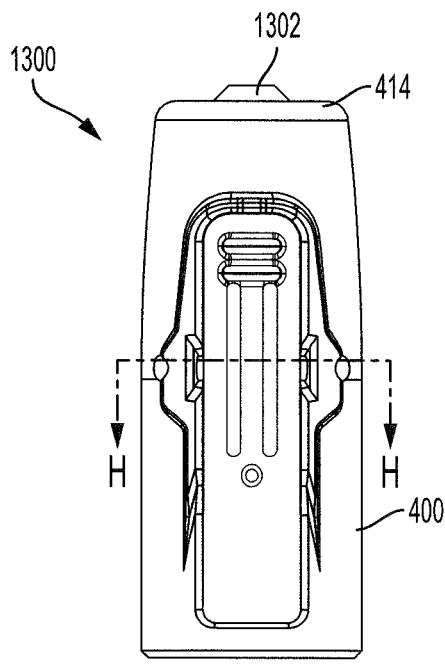
FIG. 25G is a top view of the exemplary female adapter of FIG. 25A.
Figure 25H:
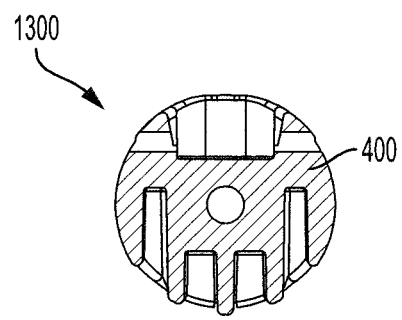
FIG. 25H is a cross-sectional view of the exemplary female adapter taken along line H-H of FIG. 25G.

Furthermore, and as embodied herein, hood 740 can have a U-shaped surface 744 sized to receive a portion of the percutaneous tubing 110. Referring now to FIGS. 20-21, as embodied herein, with the percutaneous tubing extending along the channel 715, hood 740 can be slidable between an open position, as shown in FIG. 20, with the bumper freely moveable relative to the percutaneous tubing, and a closed position, as shown in FIG. 21, with the bumper 700 secured relative to the percutaneous tubing 110. As such, in the open position, bumper 700 can be rotated freely about and moved along percutaneous tubing 110, which can allow the percutaneous tubing 110 to be directed from bumper 700 in any direction along flat surface 702. In the closed position, the U-shaped surface 744 of the hood 740 can overlap at least a portion of support wall 718 such that hood 740 can enclose a portion of the percutaneous tubing 110 within channel 715 and thus guide the percutaneous tubing 110 extending from the aperture 712 to the desired angle, e.g., a position proximate to and substantially parallel with the flat surface of base 702. In this manner, in the closed position, percutaneous tubing 110 can be disposed at an angle of about 90° relative to the exit direction of percutaneous tubing 110 from the stoma when in situ.

Any suitable fabrication technique can be used to form any of the tubing assembly and related components including, but not limited to, injection molding, milling or the like. The tubing assembly and related components can be formed of any suitable material including resilient polymers, for example but not limited to, thermoplastics, thermosets, elastomers and synthetic fibers or the like. The bumper can include, for example and without limitation, injection molded resin (e.g., MABS) and can include a TPE overmold.

Additionally, and as embodied herein, the bumper 700 can include a cushion 730 disposed along the percutaneous tubing 110 inside the body of the patient, and thus disposed on an opposing side of the stoma from the bumper 700. As such, cushion 730 can provide a flexible anchor to retain a portion of the percutaneous tubing 110 within the body. Cushion 730 can be made of a soft and flexible material compared to the bumper 700, for example a polymeric material, and can have a silicon overmold.

According to another aspect, the disclosed subject matter includes various adapters to provide connectivity between the tubing system described herein and other tubing systems or devices. For purpose of illustration and not limitation, any number of suitable adapter configurations can be used to join the male connectors and/or female connectors described herein to any other tubing system or device. For example and not limitation, adapters described herein can provide connectivity between the tubing system described herein and other tubing systems or devices having conventional connectors commercially available or otherwise known or used in the art.

For purpose of illustration and not limitation, FIGS. 22A-22F illustrate an exemplary male adapter 1000. As embodied herein, adapter 1000 can generally include a connector fitting 1002 at a first end and a second plug end 656 at a second end. For example, and as embodied herein, the second plug end 656 of adapter 1000 can have any combination of features described herein with the second plug end 656 of male connector assembly 600. Additionally or alternatively, the second plug end of adapter 1000 can be configured to have any combination of features of the second plug end 256 of male connector assembly 200.

Figure 16A:
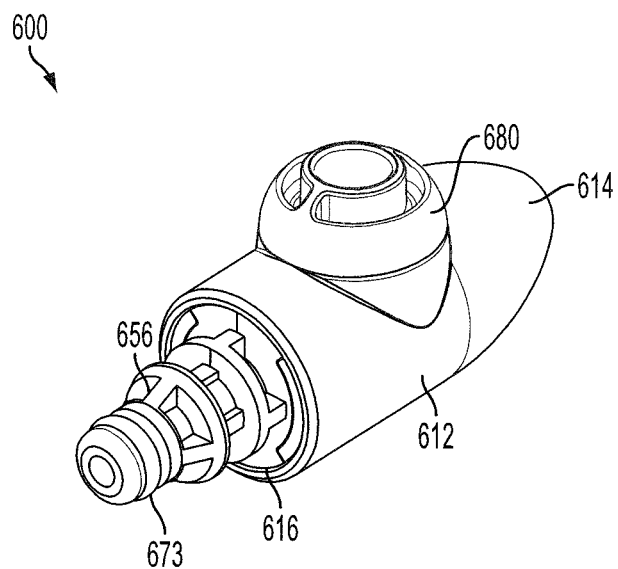
FIG. 16A is a top perspective view of another embodiment of an exemplary male connector assembly of the exemplary tubing system of FIG. 1.
Figure 16B:
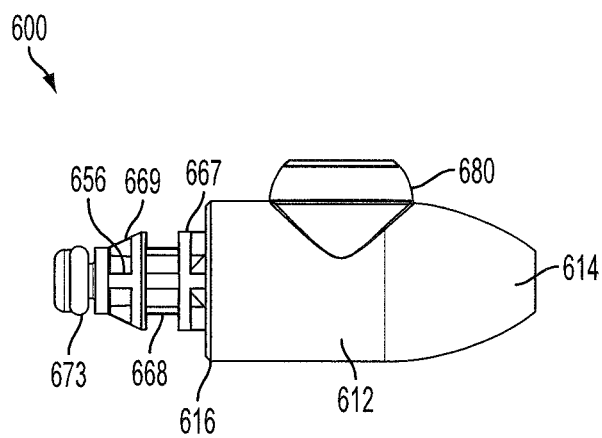
FIG. 16B is a side view of the exemplary male connector assembly of FIG. 16A.
Figure 16C:
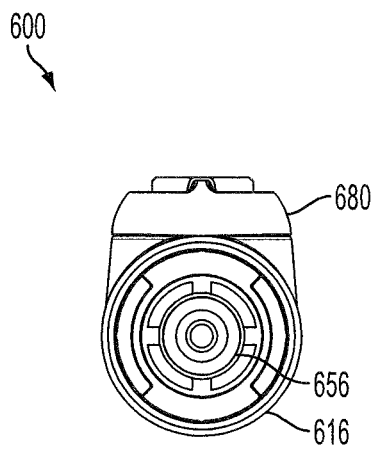
FIG. 16C is a front view of the exemplary male connector assembly of FIG. 16A.
Figure 16D:
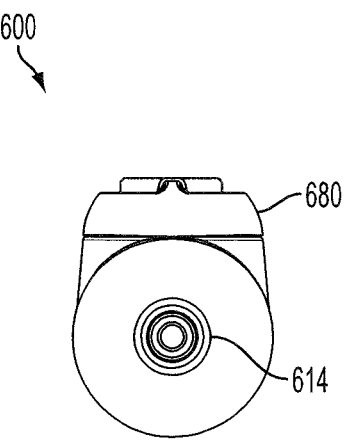
FIG. 16D is a rear view of the exemplary male connector assembly of FIG. 16A.

For example, and as shown in FIGS. 16A-16C, the second plug end 656 can define a connector to couple with device connector 400 to join adapter 1000 to a fluid source. The second plug end 656 can include a ring portion 667 and a frustoconical portion 669 defining a groove 668 therebetween. Groove 668 thus can facilitate an engagement between a device connector 400 and adapter 1000, as discussed further herein. Additionally, with reference to FIGS. 17A-17C, an open plug nub 663 can extend from the frustoconical portion 669 to define a second groove 661 therebetween. Second groove 661 can be sized to receive a gasket 673 to provide a seal between the plug 650 and the device connector 400.

Additionally, and as embodied herein, adapter 1000 can include a connector fitting 1002 configured as any suitable connector fitting to join a tubing system to device connector 400. For example and without limitation, and as depicted in FIGS. 22A-22F, connector fitting 1002 can be configured as a conventional female ENFit connector to join to a tubing system having a conventional male ENFit connector. In this manner, for purpose of illustration and not limitation, adapter 1000 can be used to join a tubing system having a conventional male ENFit connector to a fluid source, such as a syringe 430 or pump device 450 having a device connector 400, as shown for example in FIG. 1.

Furthermore, and as embodied herein, adapter 1000 can include a peripheral flange 1004 disposed between connector fitting 1002 and second plug end 656. Peripheral flange 1004 can extend from the perimeter of the remainder of adapter 1000 and can have any suitable shape to facilitate gripping of peripheral flange 1004 for joining to connectors at each end. For example, and as embodied herein, peripheral flange 1004 can be clover-shaped in end view, and thus can include indentations to facilitate gripping of peripheral flange 1004. Alternatively, peripheral flange 1004 can be ring-shaped, triangular, box-shaped or any other suitable shape.

For purpose of illustration and not limitation, FIGS. 23A-23F illustrate another exemplary male adapter 1100. As embodied herein, adapter 1100 can generally include a connector fitting 1102 at a first end and a second plug end 656 at a second end. For example, and as embodied herein, the second plug end 656 of adapter 1100 can have any combination of features described herein with the second plug end 656 of male connector assembly 600. Additionally or alternatively, the second plug end of adapter 1100 can be configured to have any combination of features of the second plug end 256 of male connector assembly 200.

For example, and as shown in FIGS. 16A-16C, the second plug end 656 can define a connector to couple with device connector 400 to join adapter 1100 to a fluid source. The second plug end 656 can include a ring portion 667 and a frustoconical portion 669 defining a groove 668 therebetween. Groove 668 thus can facilitate an engagement between a device connector 400 and adapter 1100, as discussed further herein. Additionally, with reference to FIGS. 17A-17C, an open plug nub 663 can extend from the frustoconical portion 669 to define a second groove 661 therebetween. Second groove 661 can be sized to receive a gasket 673 to provide a seal between the plug 650 and the device connector 400.

Additionally, and as embodied herein, adapter 1100 can include a connector fitting 1102 configured as any suitable connector fitting to join a tubing system to a device connector 400. For example and without limitation, and as depicted in FIGS. 23A-23F, connector fitting 1102 can be configured as a conventional female reverse Luer (e.g., ISO 594) connector to join to a conventional male reverse Luer connector. In this manner, for purpose of illustration and not limitation, adapter 1100 can be used to join a tubing system having a conventional male reverse Luer connector to a fluid source, such as a syringe 430 or pump device 450 having a device connector 400, as shown for example in FIG. 1.

Furthermore, and as embodied herein, adapter 1100 can include a peripheral flange 1104 disposed between connector fitting 1102 and second plug end 656. Peripheral flange 1104 can extend from the perimeter of the remainder of adapter 1100 and can have any suitable shape to facilitate gripping of peripheral flange 1104 for joining to connectors at each end. For example, and as embodied herein, peripheral flange 1104 can be clover-shaped, and thus can include indentations to facilitate gripping of peripheral flange 1104. Alternatively, peripheral flange 1104 can be ring-shaped, triangular, box-shaped or any other suitable shape.

Additionally or alternatively, for purpose of illustration and not limitation, adapters 1000 and 1100 can be configured with any suitable standard or non-standard connector fitting 1002 or 1102 to join a tubing system to device connector 400. For example and without limitation, connector fitting 1002 or 1102 can be configured as a standard connector, referred to herein as any ISO standard enteral connector (e.g., ISO 80369-3 Connector), ENFit connector or Luer connector to join a tubing system to device connector 400. Alternatively, connector fitting 1002 or 1102 can be configured as a non-standard connector, referred to herein as any non-ISO standard enteral connector or other standard connector listed above suitable to join a tubing system to device connector 400.

For purpose of illustration and not limitation, FIGS. 24A-24H illustrate another exemplary female adapter 1200. As embodied herein, adapter 1200 can generally include a device connector 400 with connector fitting 1202 extending from first end 414. For example, and as embodied herein, the device connector 400 can have any combination of features described herein.

For example, and as shown in FIGS. 13A-15, the device connector 400 can include a sidewall 412 defining an interior of thereof and a first end 414. Device connector 400 can have a second end 416 with an aperture therein sized and configured to receive second plug end 256 of the connector assembly 200 or second plug end 656 of connector assembly 600 in sealing engagement. The device connector 400 and/or the connector assembly 200 or 600 can be provided with a releasable connection feature to join the device connector 400 to the connector assembly 200 or 600. A variety of quick connectors can be used, such as a lever 470, as embodied herein. Lever 470 can be hingedly joined to sidewall 412 by lever projections 472 received in apertures 474 in sidewall 412. Lever 470 can also include a locking extension 476 to engage a mating portion of connector assembly 200 or 600, such as second plug end 256 or 656, respectively, as described herein. Lever 470 can thus provide a releasable engagement for device connector 400 to connector assembly 200 or 600.

As shown for example in FIG. 14, device connector 400 can further include a biasing plate 488 disposed along ramped surface 469 in the interior of device connector 400. Biasing plate 488 can be disposed within slot 478 of lever 470 to bias locking extension 476 into a locking position. Biasing plate 488 can include one or more notches 489 on one or more ends thereof, which can be sized and configured to receive a corresponding projection on lever 470, for example to align biasing plate 488 with locking extension 476 and/or free end 473. For example, and as embodied herein, as shown in FIG. 13E, in the locking position, locking extension 476 can be biased into alignment with the second end 416 aperture of device connector 400. In this configuration, when second plug end 256 or 656 of a connector assembly 200 or 600 is inserted into the second end 416 aperture of device connector 400, locking extension 476 of the lever can cam along frustoconical portion 269 or 669 of the second plug end 256 or 656 and insert into groove 268 or 668 of the second plug end, as shown for example in FIG. 15. In this manner, as embodied herein, locking extension 476 can join device connector 400 axially with connector assembly 200 or 600 with percutaneous tubing 110 for fluid communication with the interior of device connector 400 and tubing 410. Additionally, as embodied herein, locking extension 476 can be free to slide along the circumference of groove 268 or 668, and thus device connector 400 can rotate relative connector assembly 200 or 600 while remaining in axial engagement.

With reference to FIG. 14, lever 470 can have a free end 473 opposite locking extension 476. To disconnect device connector 400 from connector assembly 200, pressure can be applied to urge free end 473 at least partially within sidewall 412 to overcome the bias force of biasing plate 488 and move locking extension 476 out of alignment with second end 416 aperture of device connector 400, and thus out of groove 268 or 668 of second plug end 256 or 656. In this configuration, connector assembly 200 is free to be removed from device connector 400.

Additionally, and as embodied herein, adapter 1200 can include a connector fitting 1202 extending from first end 414 of device connector 400 and configured as any suitable connector fitting to join a tubing system or device to male connector assembly 200 or 600. For example and without limitation, and as depicted in FIGS. 24A-24H, adapter 1200 can include a connector fitting 1202 configured as a conventional female reverse Luer (e.g., ISO 594) connector to join to a conventional male reverse Luer connector. In this manner, for purpose of illustration and not limitation, adapter 1200 can be used to join a fluid source, such as syringe 430 (as shown for example in FIG. 1) having a conventional male reverse Luer connector to male connector assembly 200 or 600, which can be used for example to flush an inner J-tube 114 joined to male connector assembly 200 or 600, as shown for example in FIGS. 5-8. Additionally or alternatively, and as embodied herein, adapter 1200 can be used to join any suitable device, such as syringe 430 or pump device 450 (as shown for example in FIG. 1) having a conventional male reverse Luer connector to male connector assembly 200 or 600, for use with a tubing assembly 110 joined thereto.

Additionally or alternatively, for purpose of illustration and not limitation, adapters 1200 can be configured with any suitable standard or non-standard connector fitting 1202 to join a tubing system or device to male connector assembly 200 or 600, and a tubing system 110 joined thereto. For example and without limitation, connector fitting 1202 can be configured as an ISO standard enteral connector (e.g., ISO 80369-3 Connector), ENFit connector, Luer connector or any other standardized connector to join a tubing system or device to male connector assembly 200 or 600 and a tubing system 110 joined thereto. Alternatively, connector fitting 1202 can be configured as a non-standard connector, referred to herein as any non-ISO standard enteral connector or other standard connector listed above suitable to join a tubing system to male connector assembly 200 or 600 and a tubing system 110 joined thereto.

For purpose of illustration and not limitation, FIGS. 25A-25H illustrate another exemplary male adapter 1300. As embodied herein, adapter 1300 can generally include a device connector 400 with connector fitting 1302 extending from first end 414. For example, and as embodied herein, the device connector 400 can have any combination of features described herein.

For example, and as shown in FIGS. 13A-15, the device connector 400 can include a sidewall 412 defining an interior of thereof and a first end 414. Device connector 400 can have a second end 416 with an aperture therein sized and configured to receive second plug end 256 of the connector assembly 200 or second plug end 656 of connector assembly 600 in sealing engagement. The device connector 400 and/or the connector assembly 200 or 600 can be provided with a releasable connection feature to join the device connector 400 to the connector assembly 200 or 600. A variety of quick connectors can be used, such as a lever 470, as embodied herein. Lever 470 can be hingedly joined to sidewall 412 by lever projections 472 received in apertures 474 in sidewall 412. Lever 470 can also include a locking extension 476 to engage a mating portion of connector assembly 200 or 600, such as second plug end 256 or 656, respectively, as described herein. Lever 470 can thus provide a releasable engagement for device connector 400 to connector assembly 200 or 600.

As shown for example in FIG. 14, device connector 400 can further include a biasing plate 488 disposed along a ramped surface 469 in the interior of device connector 400. Biasing plate 488 can be disposed within slot 478 of lever 470 to bias locking extension 476 into a locking position. Biasing plate 488 can include one or more notches 489 on one or more ends thereof, which can be sized and configured to receive a corresponding projection on lever 470, for example to align biasing plate 488 with locking extension 476 and/or free end 473. For example, and as embodied herein, as shown in FIG. 13E, in the locking position, locking extension 476 can be biased into alignment with the second end 416 aperture of device connector 400. In this configuration, when second plug end 256 or 656 of a connector assembly 200 or 600 is inserted into the second end 416 aperture of device connector 400, locking extension 476 of the lever can cam along frustoconical portion 269 or 669 of the second plug end 256 or 656 and insert into groove 268 or 668 of the second plug end, as shown for example in FIG. 15. In this manner, as embodied herein, locking extension 476 can join device connector 400 axially with connector assembly 200 or 600 with percutaneous tubing 110 for fluid communication with the interior of device connector 400 and tubing 410. Additionally, as embodied herein, locking extension 476 can be free to slide along the circumference of groove 268 or 668, and thus device connector 400 can rotate relative connector assembly 200 or 600 while remaining in axial engagement.

With reference to FIG. 14, lever 470 can have a free end 473 opposite locking extension 476. To disconnect device connector 400 from connector assembly 200, pressure can be applied to urge free end 473 at least partially within sidewall 412 to overcome the bias force of biasing plate 488 and move locking extension 476 out of alignment with second end 416 aperture of device connector 400, and thus out of groove 268 or 668 of second plug end 256 or 656. In this configuration, connector assembly 200 is free to be removed from device connector 400.

Additionally, and as embodied herein, adapter 1300 can include a connector fitting 1302 extending from first end 414 of device connector 400 and configured as any suitable connector fitting to join a tubing system or device to male connector assembly 200 or 600. For example and without limitation, and as depicted in FIGS. 25A-25H, adapter 1200 can include a connector fitting 1302 configured as a conventional male ENFit connector to join to a conventional female ENFit connector. In this manner, for purpose of illustration and not limitation, adapter 1300 can be used to join a fluid source, such as syringe 430 (as shown for example in FIG. 1) having a conventional female ENFit connector to male connector assembly 200 or 600, which can be used for example to flush an inner J-tube 114 joined to male connector assembly 200 or 600, as shown for example in FIGS. 5-8. Additionally or alternatively, and as embodied herein, adapter 1300 can be used to join any suitable device, such as syringe 430 or pump device 450 (as shown for example in FIG. 1) having a conventional female ENFit connector to male connector assembly 200 or 600, for use with a tubing assembly 110 joined thereto.

Additionally or alternatively, for purpose of illustration and not limitation, adapters 1300 can be configured with any suitable standard or non-standard connector fitting 1302 to join a tubing system or device to male connector assembly 200 or 600, and a tubing system 110 joined thereto. For example and without limitation, connector fitting 1302 can be configured as an ISO standard enteral connector (e.g., ISO 80369-3 Connector), ENFit connector, Luer connector or any other standardized connector to join a tubing system or device to male connector assembly 200 or 600 and a tubing system 110 joined thereto. Alternatively, connector fitting 1302 can be configured as a non-standard connector, referred to herein as any non-ISO standard enteral connector or other standard connector listed above suitable to join a tubing system to male connector assembly 200 or 600 and a tubing system 110 joined thereto.

According to other aspects of the disclosed subject matter, a connector kit for percutaneous tubing is provided. The kit generally includes a female connector and a male adapter. The female connector has a first end and a second end and includes a lever having a locking extension proximate the first end. The female connector is configured to be joined to a fluid source proximate the second end. The male adapter has a first end and a second end and includes a connector fitting proximate the first end, the connector fitting configured to join to a connector for a percutaneous tubing system. The male adapter also includes a male connector proximate the second end, the male connector including a plug end with a fluid lumen defined therethrough. The plug end has a circumferential groove defined therein to receive the locking extension of the female connector to allow the female connector to rotate relative to and maintain axial engagement with the male connector when the locking extension is received within the circumferential groove.

As embodied herein, a kit can include a female connector, such as a device connector 400, which can be configured to be joined to a fluid source, for example and without limitation, syringe 430 and/or pump device 450, as described herein. Additionally, for purpose of illustration and without limitation, the kit can include a male adapter, such as male adapter 1000 or 1100, to join to the female connector, such as device connector 400, as described herein. Device connector 400 and male adapters 1000 or 1100 can include any combination of features described herein.

According to other aspects of the disclosed subject matter, a connector kit for percutaneous tubing is provided. The percutaneous tubing includes an outer G-tube and an inner J-tube. The kit generally includes a male connector and a female adapter. The male connector includes a shell having a sidewall defining an interior, a first shell end having a first opening defined therein, and a second shell end having a second opening defined therein, each of the first and second openings in communication with the interior to receive the percutaneous tubing therethrough, the shell further having an engagement portion, a connector body having a first body end and a second body end with a tube lumen defined therethrough, the first body end having a connector tip sized to receive the inner J-tube therethrough and mate with the outer G-tube, the connector body having an engaging portion to engage the engagement portion of the shell, and a plug configured to be joined to the connector body and having a first plug end and a second plug end with a fluid lumen defined therethrough, the first plug end having a plug tip extending therefrom, the tip sized to mate with the inner J-tube. The female adapter has a first end and a second end and includes a connector fitting proximate the first end, the connector fitting configured to join to a connector for a fluid source. The female adapter also includes a female connector proximate the second end, the female connector comprising a lever having a locking extension, the locking extension sized to be received within the groove defined in the second plug end of the male connector to allow the female connector to rotate relative to and maintain axial engagement with the male connector when the locking extension is received within the groove.

As embodied herein, a kit can include a male connector, such as a connector assembly 200 or 600, which can be configured to be joined, for example and without limitation, to percutaneous tubing 110, as described herein. Additionally, for purpose of illustration and without limitation, the kit can include a female adapter, such as female adapter 1200, to join to the male connector, such as connector assembly 200 or 600, as described herein. Connector assembly 200 or 600 and female adapter 1200 can include any combination of features described herein.

Alternatively, and as embodied herein, a kit can include a male connector, such as a connector assembly 200 or 600, which can be configured to be joined, for example and without limitation, to percutaneous tubing 110, as described herein. Additionally, for purpose of illustration and without limitation, the kit can include a male adapter, such as male adapter 1300, to join to the male connector, such as connector assembly 200 or 600, as described herein. Connector assembly 200 or 600 and male adapter 1300 can include any combination of features described herein.

The connector assembly, tubing system, adapters and connector kits of the disclosed subject matter can be used for delivery of any of a variety of suitable fluid substances of corresponding volume or dose.

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A connector kit for percutaneous tubing, the kit comprising:
a female connector having a first end, a second end and a sidewall, the female connector comprising a lever having a locking extension proximate the first end, the female connector configured to be joined to a fluid source proximate the second end, the lever further comprising a free end configured to be urged at least partially within the sidewall to overcome a bias force of a biasing plate of the female connector and thereby move the locking extension from alignment with an aperture proximate the second end of the female connector and release the locking extension from engagement with the groove of the male connector; and
a male adapter having a first end and a second end, the adapter comprising:
a connector fitting proximate the first end, the connector fitting configured to join to a connector for a percutaneous tubing system, and
a male connector proximate the second end, the male connector comprising a plug end with a fluid lumen defined therethrough, the plug end having a circumferential groove defined therein configured to receive the locking extension of the female connector to allow the female connector to rotate relative to and maintain axial engagement with the male connector without axial displacement when the locking extension is received within the circumferential groove.

2. The connector kit of claim 1, wherein the connector fitting is configured to join to a standard connector.

3. The connector kit of claim 1, wherein the connector fitting is configured to join to a non-standard connector.

4. The connector kit of claim 1, wherein the connector fitting comprises a female connector to join to the tubing system or the device.

5. The connector kit of claim 1, wherein the connector fitting comprises a Luer connector.

6. The connector kit of claim 1, wherein the connector fitting comprises a female reverse Luer connector.

7. The connector kit of claim 1, further comprising a peripheral flange disposed between the first end and the second end.

8. The connector kit of claim 7, wherein the peripheral flange is clover shaped in end view.

9. A female adapter for a connector assembly for percutaneous tubing, the female adapter having a first end, a second end and a sidewall, the female adapter comprising:
a connector fitting proximate the first end, the connector fitting configured to join to a connector for a tubing system or device; and
a female connector proximate the second end, the female connector comprising a lever having a locking extension, the locking extension sized to be received within a groove defined in a male plug end of a male connector to allow the female connector to rotate relative to and maintain axial engagement with the male connector without axial displacement when the locking extension is received within the groove, the lever further comprising a free end opposite the locking extension, the free end configured to be urged at least partially within the sidewall to overcome a bias force of a biasing plate of the female connector and move the locking extension from alignment with an aperture proximate the second end of the female connector and release the locking extension from engagement with the groove of the male connector.

10. The female adapter of claim 9, wherein the connector fitting is configured to join to a standard connector.

11. The female adapter of claim 9, wherein the connector fitting is configured to join to a non-standard connector.

12. The female adapter of claim 9, wherein the connector fitting comprises a connector to join to the tubing system or the device.

13. The female adapter of claim 9, wherein the connector fitting comprises a Luer connector.

14. The female adapter of claim 9, wherein the connector fitting comprises a male reverse Luer connector.

15. The female adapter of claim 9, wherein the connector fitting is configured to receive a syringe to flush an inner J-tube of a percutaneous tubing system when joined to the female connector.

16. A connector kit for percutaneous tubing, the percutaneous tubing including an outer G-tube and an inner J-tube, the kit comprising:
   a male connector comprising:
      a shell having a sidewall defining an interior, a first shell end having a first opening defined therein, and a second shell end having a second opening defined therein, each of the first and second openings in communication with the interior to receive the percutaneous tubing therethrough, the shell further having an engagement portion,
      a connector body having a first body end and a second body end with a tube lumen defined therethrough, the first body end having a connector tip sized to receive the inner J-tube therethrough and mate with the outer G-tube, the connector body having an engaging portion to engage the engagement portion of the shell, and
      a plug configured to be joined to the connector body and having a first plug end and a second plug end with a fluid lumen defined therethrough, the first plug end having a plug tip extending therefrom, the tip sized to mate with the inner J-tube; and
   a female adapter having a first end and a second end, the adapter comprising:
      a connector fitting proximate the first end, the connector fitting configured to join to a connector for a fluid source, and
      a female connector proximate the second end, the female connector comprising a lever having a locking extension, the locking extension sized to be received within the groove defined in the second plug end of the male connector to allow the female connector to rotate relative to and maintain axial engagement with the male connector without axial displacement when the locking extension is received within the groove.

\* \* \* \* \*